United States Patent
Kleiner et al.

(10) Patent No.: US 8,906,028 B2
(45) Date of Patent: Dec. 9, 2014

(54) BONE GRAFT DELIVERY DEVICE AND METHOD OF USING THE SAME

(75) Inventors: Jeffrey Kleiner, Aurora, CO (US); Edward John Grimberg, Jr., Golden, CO (US)

(73) Assignee: Spinal Surgical Strategies, LLC, Denver, CO (US)

(*) Notice: Subject to any disclaimer, the term of this patent is extended or adjusted under 35 U.S.C. 154(b) by 98 days.

(21) Appl. No.: 12/886,452

(22) Filed: Sep. 20, 2010

(65) Prior Publication Data

US 2011/0071536 A1   Mar. 24, 2011

Related U.S. Application Data

(60) Provisional application No. 61/243,664, filed on Sep. 18, 2009.

(51) Int. Cl.
| | | |
|---|---|---|
| A61B 17/56 | (2006.01) | |
| A61F 2/46 | (2006.01) | |
| A61F 2/30 | (2006.01) | |
| A61F 2/44 | (2006.01) | |

(52) U.S. Cl.
CPC ..... *A61F 2/4601* (2013.01); *A61F 2002/30153* (2013.01); *A61F 2/4455* (2013.01); *A61F 2002/30601* (2013.01); *A61F 2230/0019* (2013.01); *A61F 2002/4602* (2013.01)
USPC ................. 606/93; 606/92; 606/94

(58) Field of Classification Search
USPC ............. 606/92–94, 99; 623/17.11, 17.16; 604/15, 57, 187, 218, 231
See application file for complete search history.

(56) References Cited

U.S. PATENT DOCUMENTS

| | | |
|---|---|---|
| D30,951 S | 6/1899 | Saint Cyr, Jr. |
| 1,867,624 A | 7/1932 | Hoffman |
| 2,520,464 A | 8/1950 | Hubner |
| 3,697,011 A | 10/1972 | Christensen et al. |
| 3,741,496 A | 6/1973 | Beller |
| 3,836,092 A | 9/1974 | Hull |
| 3,855,638 A | 12/1974 | Pilliar |
| 4,039,156 A | 8/1977 | Abraham |
| 4,041,939 A | 8/1977 | Hall |
| 4,047,524 A | 9/1977 | Hall |
| 4,206,516 A | 6/1980 | Pilliar |
| 4,277,184 A * | 7/1981 | Solomon ................. 366/139 |
| 4,430,062 A | 2/1984 | Henrichsen et al. |
| 4,462,402 A | 7/1984 | Burgio et al. |

(Continued)

FOREIGN PATENT DOCUMENTS

| | | |
|---|---|---|
| WO | WO 99/08627 | 2/1999 |
| WO | WO 2005/037149 | 4/2005 |

OTHER PUBLICATIONS

U.S. Appl. No. 12/367,487, filed Feb. 6, 2009, Kleiner.
U.S. Appl. No. 13/168,611, filed Jun. 24, 2011, Kleiner.

(Continued)

*Primary Examiner* — Christian Sevilla
(74) *Attorney, Agent, or Firm* — Sheridan Ross P.C.

(57) ABSTRACT

The present invention relates to a device and method for delivery of bone graft material to any portion of a patient which requires bone graft material. The device according to various embodiments delivers bone graft to a bone graft receiving area. The bone graft delivery device is formed such that a hollow tube and plunger selectively and controllably place bone graft material in or adjacent to the bone graft receiving area.

16 Claims, 7 Drawing Sheets

(56) References Cited

U.S. PATENT DOCUMENTS

| | | |
|---|---|---|
| 4,467,478 A | 8/1984 | Jurgutis |
| 4,501,269 A | 2/1985 | Bagby |
| 4,522,270 A | 6/1985 | Kishi |
| 4,570,623 A | 2/1986 | Ellison et al. |
| 4,580,978 A | 4/1986 | Motola et al. |
| 4,592,346 A | 6/1986 | Jurgutis |
| 4,743,256 A | 5/1988 | Brantigan |
| 4,877,399 A | 10/1989 | Frank et al. |
| 4,925,924 A | 5/1990 | Silver et al. |
| D309,499 S | 7/1990 | Bowman et al. |
| D312,309 S | 11/1990 | Michelson |
| 4,991,570 A | 2/1991 | Bullard |
| 5,037,422 A | 8/1991 | Hayhurst |
| 5,053,038 A | 10/1991 | Sheehan |
| 5,055,104 A | 10/1991 | Ray |
| 5,058,823 A | 10/1991 | Emura et al. |
| 5,282,744 A | 2/1994 | Meyer |
| 5,290,295 A | 3/1994 | Querals et al. |
| 5,311,640 A | 5/1994 | Holland |
| 5,312,407 A | 5/1994 | Carter |
| 5,312,417 A | 5/1994 | Wilk |
| 5,324,307 A | 6/1994 | Jarrett et al. |
| 5,329,834 A | 7/1994 | Wong |
| 5,333,812 A | 8/1994 | Sato |
| D351,022 S | 9/1994 | Saito |
| 5,354,292 A | 10/1994 | Braeuer et al. |
| 5,395,372 A | 3/1995 | Holt et al. |
| 5,425,772 A | 6/1995 | Brantigan |
| D360,689 S | 7/1995 | Giampapa |
| 5,431,658 A | 7/1995 | Moskovich |
| D364,462 S | 11/1995 | Michelson |
| 5,520,611 A | 5/1996 | Rao et al. |
| D370,531 S | 6/1996 | Ash et al. |
| 5,527,312 A | 6/1996 | Ray |
| D372,311 S | 7/1996 | Koros et al. |
| 5,541,191 A | 7/1996 | Skotnicki et al. |
| D372,781 S | 8/1996 | Reif |
| 5,549,607 A | 8/1996 | Olson et al. |
| 5,554,191 A | 9/1996 | Lahille et al. |
| 5,558,674 A | 9/1996 | Heggeness et al. |
| D374,283 S | 10/1996 | Michelson |
| 5,562,661 A | 10/1996 | Yoshimi et al. |
| 5,569,246 A | 10/1996 | Ojima et al. |
| 5,586,989 A | 12/1996 | Bray |
| 5,595,563 A | 1/1997 | Moisdon |
| 5,601,557 A | 2/1997 | Hayhurst |
| D378,409 S | 3/1997 | Michelson |
| 5,611,800 A | 3/1997 | Davis et al. |
| 5,634,925 A | 6/1997 | Urbanski |
| 5,653,763 A | 8/1997 | Errico et al. |
| 5,662,655 A | 9/1997 | Laboureau et al. |
| 5,665,122 A | 9/1997 | Kambin |
| 5,683,464 A | 11/1997 | Wagner et al. |
| 5,688,285 A | 11/1997 | Yamada |
| 5,697,932 A | 12/1997 | Smith et al. |
| 5,702,449 A | 12/1997 | McKay |
| 5,704,892 A | 1/1998 | Adair |
| 5,741,253 A | 4/1998 | Michelson |
| 5,762,629 A | 6/1998 | Kambin |
| 5,779,642 A | 7/1998 | Nightengale |
| 5,782,919 A | 7/1998 | Zdeblick et al. |
| 5,797,918 A | 8/1998 | McGuire et al. |
| 5,836,948 A | 11/1998 | Zucherman et al. |
| 5,836,958 A | 11/1998 | Ralph |
| 5,860,973 A | 1/1999 | Michelson |
| 5,860,977 A | 1/1999 | Zucherman et al. |
| 5,865,746 A | 2/1999 | Murugesan et al. |
| 5,865,846 A | 2/1999 | Bryan et al. |
| 5,871,462 A | 2/1999 | Yoder et al. |
| 5,888,228 A | 3/1999 | Knothe et al. |
| 5,904,689 A | 5/1999 | Jonjic |
| 5,904,718 A | 5/1999 | Jefferies |
| 5,906,616 A | 5/1999 | Pavlov et al. |
| 5,925,051 A | 7/1999 | Mikhail |
| 5,925,056 A | 7/1999 | Thomas et al. |
| 5,944,658 A | 8/1999 | Koros et al. |
| 5,944,686 A | 8/1999 | Patterson et al. |
| 5,947,972 A | 9/1999 | Gage et al. |
| 5,976,146 A | 11/1999 | Ogawa et al. |
| 5,989,257 A | 11/1999 | Tidwell et al. |
| 5,997,895 A | 12/1999 | Narotam et al. |
| 6,004,191 A | 12/1999 | Schur et al. |
| 6,004,326 A | 12/1999 | Castro et al. |
| 6,013,028 A | 1/2000 | Jho et al. |
| 6,019,765 A * | 2/2000 | Thornhill et al. ............... 606/94 |
| 6,030,356 A | 2/2000 | Carlson et al. |
| 6,030,388 A | 2/2000 | Yoshimi et al. |
| 6,030,390 A | 2/2000 | Mehdizadeh |
| 6,030,401 A | 2/2000 | Marino |
| 6,033,408 A | 3/2000 | Gage et al. |
| 6,033,438 A | 3/2000 | Bianchi et al. |
| 6,045,555 A | 4/2000 | Smith et al. |
| 6,059,829 A | 5/2000 | Schlapfer et al. |
| 6,090,143 A | 7/2000 | Meriwether et al. |
| 6,096,080 A | 8/2000 | Nicholson et al. |
| 6,113,602 A | 9/2000 | Sand |
| 6,120,503 A | 9/2000 | Michelson |
| 6,123,705 A | 9/2000 | Michelson |
| 6,136,001 A | 10/2000 | Michelson |
| 6,142,998 A | 11/2000 | Smith et al. |
| 6,146,420 A | 11/2000 | McKay |
| 6,149,096 A | 11/2000 | Hartley |
| 6,152,871 A | 11/2000 | Foley et al. |
| 6,159,211 A | 12/2000 | Boriani et al. |
| 6,159,245 A | 12/2000 | Meriwether et al. |
| 6,180,085 B1 | 1/2001 | Achilefu |
| 6,209,886 B1 | 4/2001 | Estes et al. |
| 6,216,573 B1 | 4/2001 | Moutafis et al. |
| 6,224,599 B1 | 5/2001 | Baynham et al. |
| 6,235,805 B1 | 5/2001 | Chang et al. |
| 6,238,397 B1 | 5/2001 | Zucherman et al. |
| 6,241,733 B1 | 6/2001 | Nicholson et al. |
| 6,241,769 B1 | 6/2001 | Nicholson et al. |
| 6,245,108 B1 | 6/2001 | Biscup |
| 6,258,094 B1 | 7/2001 | Nicholson et al. |
| 6,261,293 B1 | 7/2001 | Nicholson et al. |
| 6,261,295 B1 | 7/2001 | Nicholson et al. |
| 6,261,296 B1 | 7/2001 | Aebi et al. |
| 6,290,724 B1 | 9/2001 | Marino |
| 6,299,613 B1 | 10/2001 | Ogilvie et al. |
| 6,309,395 B1 | 10/2001 | Smith et al. |
| 6,325,805 B1 | 12/2001 | Ogilvie et al. |
| 6,328,738 B1 | 12/2001 | Suddaby |
| 6,336,928 B1 | 1/2002 | Guerin et al. |
| 6,342,074 B1 | 1/2002 | Simpson |
| 6,364,880 B1 | 4/2002 | Michelson |
| 6,375,635 B1 | 4/2002 | Moutafis et al. |
| 6,387,096 B1 | 5/2002 | Hyde, Jr. |
| 6,409,765 B1 | 6/2002 | Bianchi et al. |
| 6,436,101 B1 | 8/2002 | Hamada |
| 6,451,017 B1 | 9/2002 | Moutafis et al. |
| 6,454,806 B1 | 9/2002 | Cohen et al. |
| 6,467,556 B2 | 10/2002 | Alsruhe |
| D467,657 S | 12/2002 | Scribner |
| 6,500,206 B1 | 12/2002 | Bryan |
| 6,511,493 B1 | 1/2003 | Moutafis et al. |
| D469,871 S | 2/2003 | Sand |
| 6,520,976 B1 | 2/2003 | Gage |
| 6,524,318 B1 | 2/2003 | Longhini et al. |
| 6,565,574 B2 | 5/2003 | Michelson |
| 6,569,201 B2 | 5/2003 | Moumene et al. |
| 6,613,091 B1 | 9/2003 | Zdeblick et al. |
| 6,616,669 B2 | 9/2003 | Ogilvie et al. |
| 6,620,356 B1 | 9/2003 | Wong et al. |
| 6,641,613 B2 | 11/2003 | Sennett |
| 6,648,915 B2 | 11/2003 | Sazy |
| 6,652,533 B2 | 11/2003 | O'Neil |
| 6,669,710 B2 | 12/2003 | Moutafis et al. |
| 6,673,113 B2 | 1/2004 | Ralph et al. |
| 6,679,887 B2 | 1/2004 | Nicholson et al. |
| 6,695,882 B2 | 2/2004 | Bianchi et al. |
| 6,699,288 B2 | 3/2004 | Moret |
| 6,709,438 B2 | 3/2004 | Dixon et al. |
| 6,719,760 B2 | 4/2004 | Dorchak et al. |

(56) References Cited

U.S. PATENT DOCUMENTS

| | | |
|---|---|---|
| 6,719,795 B1 | 4/2004 | Cornwall et al. |
| 6,730,125 B1 | 5/2004 | Lin |
| 6,743,257 B2 | 6/2004 | Castro |
| 6,746,487 B2 | 6/2004 | Scifert et al. |
| 6,764,491 B2 | 7/2004 | Frey et al. |
| 6,773,437 B2 | 8/2004 | Ogilvie et al. |
| 6,800,093 B2 | 10/2004 | Nicholson et al. |
| 6,824,565 B2 | 11/2004 | Muhanna et al. |
| 6,830,574 B2 | 12/2004 | Heckele et al. |
| 6,852,126 B2 | 2/2005 | Ahlgren |
| 6,869,430 B2 | 3/2005 | Balbierz et al. |
| 6,890,728 B2 | 5/2005 | Dolecek et al. |
| 6,899,712 B2 | 5/2005 | Moutafis et al. |
| 6,923,792 B2 | 8/2005 | Staid et al. |
| 6,929,646 B2 | 8/2005 | Gambale |
| 6,942,665 B2 | 9/2005 | Gambale |
| 6,960,182 B2 | 11/2005 | Moutafis et al. |
| 6,962,592 B2 | 11/2005 | Gatturna et al. |
| 6,969,523 B1 | 11/2005 | Mattern et al. |
| 6,974,480 B2 | 12/2005 | Messerli et al. |
| 6,991,653 B2 | 1/2006 | White et al. |
| 6,994,728 B2 | 2/2006 | Zubok et al. |
| 7,004,946 B2 | 2/2006 | Parker et al. |
| 7,008,431 B2 | 3/2006 | Simonson |
| 7,014,640 B2 | 3/2006 | Kemppainen et al. |
| 7,025,742 B2 | 4/2006 | Rubenstein et al. |
| 7,025,769 B1 | 4/2006 | Ferree |
| 7,033,317 B2 | 4/2006 | Pruitt |
| 7,041,136 B2 | 5/2006 | Goble et al. |
| 7,066,961 B2 | 6/2006 | Hichelson |
| 7,077,864 B2 | 7/2006 | Byrd, III et al. |
| 7,094,257 B2 | 8/2006 | Mujwid et al. |
| 7,122,017 B2 | 10/2006 | Moutafis et al. |
| 7,128,760 B2 | 10/2006 | Michelson |
| 7,135,043 B2 | 11/2006 | Nakahara et al. |
| 7,182,782 B2 | 2/2007 | Kirschman |
| 7,204,825 B2 | 4/2007 | Cimino et al. |
| 7,207,992 B2 | 4/2007 | Ritland |
| 7,211,112 B2 | 5/2007 | Baynham et al. |
| 7,214,186 B2 | 5/2007 | Ritland |
| 7,223,292 B2 | 5/2007 | Messerli et al. |
| 7,232,463 B2 | 6/2007 | Falahee |
| 7,238,203 B2 | 7/2007 | Bagga et al. |
| 7,255,703 B2 | 8/2007 | Mujwid et al. |
| 7,267,691 B2 | 9/2007 | Keller et al. |
| 7,273,498 B2 | 9/2007 | Bianchi et al. |
| 7,288,093 B2 | 10/2007 | Michelson |
| 7,316,070 B2 | 1/2008 | Green |
| 7,329,283 B2 | 2/2008 | Estes et al. |
| 7,337,538 B2 | 3/2008 | Moutafis et al. |
| 7,341,590 B2 | 3/2008 | Ferree |
| 7,341,591 B2 | 3/2008 | Grinberg |
| 7,357,284 B2 | 4/2008 | Jauvin |
| 7,357,804 B2 | 4/2008 | Binder, Jr. et al. |
| 7,361,178 B2 | 4/2008 | Hearn et al. |
| 7,364,657 B2 | 4/2008 | Mandrusov et al. |
| 7,371,239 B2 | 5/2008 | Dec et al. |
| 7,377,923 B2 | 5/2008 | Purcell et al. |
| 7,387,643 B2 | 6/2008 | Michelson |
| 7,399,041 B2 | 7/2008 | Prentner et al. |
| D574,495 S | 8/2008 | Petersen |
| 7,406,775 B2 | 8/2008 | Funk et al. |
| 7,410,334 B2 | 8/2008 | McGrew |
| 7,410,478 B2 | 8/2008 | Yang |
| 7,413,065 B2 | 8/2008 | Gauthier |
| 7,421,772 B2 | 9/2008 | Gao et al. |
| 7,429,270 B2 | 9/2008 | Baumgartner et al. |
| D579,562 S | 10/2008 | Anderson et al. |
| 7,430,945 B2 | 10/2008 | Gauthier et al. |
| 7,431,711 B2 | 10/2008 | Moutafis et al. |
| 7,442,208 B2 | 10/2008 | Mathieu et al. |
| 7,455,157 B2 | 11/2008 | Kimes et al. |
| D582,552 S | 12/2008 | Berberich |
| 7,461,803 B2 | 12/2008 | Boerner |
| 7,473,255 B2 | 1/2009 | McGarity et al. |
| 7,476,226 B2 | 1/2009 | Weikel et al. |
| 7,478,577 B1 | 1/2009 | Wheeler |
| 7,481,766 B2 | 1/2009 | Lee et al. |
| 7,481,813 B1 | 1/2009 | Purcell |
| 7,485,145 B2 | 2/2009 | Purcell |
| D589,626 S | 3/2009 | Petersen |
| 7,501,073 B2 | 3/2009 | Wen et al. |
| 7,503,933 B2 | 3/2009 | Michelson |
| 7,503,934 B2 | 3/2009 | Eisermann et al. |
| 7,503,936 B2 | 3/2009 | Trieu |
| D590,943 S | 4/2009 | Petersen |
| D590,945 S | 4/2009 | Berberich |
| 7,513,901 B2 | 4/2009 | Scifert et al. |
| D593,202 S | 5/2009 | Petersen |
| 7,531,003 B2 | 5/2009 | Reindel |
| 7,534,265 B1 | 5/2009 | Boyd |
| 7,534,270 B2 | 5/2009 | Ball |
| D594,119 S | 6/2009 | Berberich et al. |
| 7,553,320 B2 | 6/2009 | Molz, IV et al. |
| D597,669 S | 8/2009 | Petersen |
| D598,096 S | 8/2009 | Petersen |
| D599,015 S | 8/2009 | Petersen |
| 7,578,820 B2 | 8/2009 | Moore et al. |
| D600,806 S | 9/2009 | Horton et al. |
| D601,251 S | 9/2009 | Horton et al. |
| 7,582,058 B1 | 9/2009 | Miles et al. |
| 7,582,107 B2 | 9/2009 | Trail et al. |
| 7,595,043 B2 | 9/2009 | Hedrick et al. |
| D603,502 S | 11/2009 | Petersen |
| 7,615,078 B2 | 11/2009 | White et al. |
| 7,618,423 B1 | 11/2009 | Valentine et al. |
| 7,625,374 B2 | 12/2009 | Branch et al. |
| 7,632,276 B2 | 12/2009 | Fishbein |
| D608,001 S | 1/2010 | Reardon et al. |
| 7,655,027 B2 | 2/2010 | Michelson |
| 7,658,766 B2 | 2/2010 | Melkent et al. |
| 7,671,014 B2 | 3/2010 | Beals et al. |
| 7,674,297 B2 | 3/2010 | Falahee |
| 7,677,418 B2 | 3/2010 | Henniges et al. |
| 7,686,805 B2 | 3/2010 | Michelson |
| 7,691,133 B2 | 4/2010 | Partin et al. |
| 7,693,562 B2 | 4/2010 | Marino et al. |
| 7,699,852 B2 | 4/2010 | Frankel et al. |
| 7,708,761 B2 | 5/2010 | Petersen |
| 7,717,685 B2 | 5/2010 | Moutafis et al. |
| 7,722,530 B2 | 5/2010 | Davison |
| 7,722,613 B2 | 5/2010 | Sutterlin et al. |
| 7,723,291 B2 | 5/2010 | Beals et al. |
| 7,728,868 B2 | 6/2010 | Razzaque et al. |
| 7,730,563 B1 | 6/2010 | Sklar et al. |
| 7,734,327 B2 | 6/2010 | Colquhoun |
| 7,740,634 B2 | 6/2010 | Orbay et al. |
| 7,740,661 B2 | 6/2010 | Baratz et al. |
| 7,744,555 B2 | 6/2010 | DiMauro et al. |
| 7,744,637 B2 | 6/2010 | Johnson et al. |
| 7,744,973 B2 | 6/2010 | Schoenle et al. |
| D620,108 S | 7/2010 | Eitenmueller et al. |
| 7,749,231 B2 | 7/2010 | Bonvallet et al. |
| 7,749,253 B2 | 7/2010 | Zucherman et al. |
| 7,749,269 B2 | 7/2010 | Peterman et al. |
| 7,749,273 B2 | 7/2010 | Cauthen et al. |
| 7,749,274 B2 | 7/2010 | Razian |
| 7,749,276 B2 | 7/2010 | Fitz |
| 7,749,279 B2 | 7/2010 | Twomey et al. |
| 7,749,555 B2 | 7/2010 | Zanella |
| 7,751,865 B2 | 7/2010 | Jascob et al. |
| 7,753,911 B2 | 7/2010 | Ray et al. |
| 7,753,914 B2 | 7/2010 | Ruhling et al. |
| 7,753,938 B2 | 7/2010 | Aschmann et al. |
| 7,753,940 B2 | 7/2010 | Veldman et al. |
| 7,753,962 B2 | 7/2010 | Melder |
| 7,758,501 B2 | 7/2010 | Frasier et al. |
| 7,758,616 B2 | 7/2010 | LeHuec et al. |
| 7,758,617 B2 | 7/2010 | Iott et al. |
| 7,758,644 B2 | 7/2010 | Trieu |
| 7,758,648 B2 | 7/2010 | Castleman et al. |
| 7,763,025 B2 | 7/2010 | Assell et al. |
| 7,763,035 B2 | 7/2010 | Melkent et al. |
| 7,763,055 B2 | 7/2010 | Foley |

(56) References Cited

U.S. PATENT DOCUMENTS

| | | |
|---|---|---|
| 7,763,078 B2 | 7/2010 | Peterman et al. |
| 7,763,080 B2 | 7/2010 | Southworth |
| D621,509 S | 8/2010 | Lovell |
| D622,395 S | 8/2010 | Iott et al. |
| D622,843 S | 8/2010 | Horton |
| D622,851 S | 8/2010 | Horton |
| 7,766,914 B2 | 8/2010 | McCormack et al. |
| 7,766,918 B2 | 8/2010 | Allard et al. |
| 7,766,930 B2 | 8/2010 | DiPoto et al. |
| 7,766,940 B2 | 8/2010 | Kwak et al. |
| 7,766,967 B2 | 8/2010 | Francis |
| 7,766,969 B2 | 8/2010 | Justin et al. |
| 7,769,422 B2 | 8/2010 | DiSilvestro et al. |
| 7,771,143 B2 | 8/2010 | Bharadwaj et al. |
| 7,771,475 B2 | 8/2010 | Michelson |
| 7,771,476 B2 | 8/2010 | Justis et al. |
| 7,771,479 B2 | 8/2010 | Humphreys et al. |
| 7,776,040 B2 | 8/2010 | Markworth et al. |
| 7,776,046 B2 | 8/2010 | Boyd et al. |
| 7,776,047 B2 | 8/2010 | Fanger et al. |
| 7,776,049 B1 | 8/2010 | Curran et al. |
| 7,776,075 B2 | 8/2010 | Bruneau et al. |
| 7,776,090 B2 | 8/2010 | Winslow et al. |
| 7,776,091 B2 | 8/2010 | Mastrorio et al. |
| 7,776,094 B2 | 8/2010 | McKinley et al. |
| 7,776,095 B2 | 8/2010 | Peterman et al. |
| 7,776,594 B2 | 8/2010 | Bays et al. |
| 7,780,707 B2 | 8/2010 | Johnson et al. |
| 7,794,396 B2 | 9/2010 | Gattani et al. |
| 7,794,501 B2 | 9/2010 | Edie et al. |
| 7,799,034 B2 | 9/2010 | Johnson et al. |
| 7,799,036 B2 | 9/2010 | Davison et al. |
| 7,799,053 B2 | 9/2010 | Haid et al. |
| 7,799,054 B2 | 9/2010 | Kwak et al. |
| 7,799,055 B2 | 9/2010 | Lim |
| 7,799,056 B2 | 9/2010 | Sankaran |
| 7,799,076 B2 | 9/2010 | Sybert et al. |
| 7,799,078 B2 | 9/2010 | Embry et al. |
| 7,799,083 B2 | 9/2010 | Smith et al. |
| 7,806,901 B2 | 10/2010 | Stad et al. |
| 7,811,327 B2 | 10/2010 | Hansell et al. |
| 7,811,329 B2 | 10/2010 | Ankney et al. |
| 7,815,681 B2 | 10/2010 | Ferguson |
| 7,819,801 B2 | 10/2010 | Miles et al. |
| D627,460 S | 11/2010 | Horton |
| 7,824,328 B2 | 11/2010 | Gattani et al. |
| 7,824,332 B2 | 11/2010 | Fakhrai |
| 7,824,410 B2 | 11/2010 | Simonson |
| 7,824,703 B2 | 11/2010 | Scifert et al. |
| 7,828,804 B2 | 11/2010 | Li et al. |
| 7,828,845 B2 | 11/2010 | Estes et al. |
| 7,828,849 B2 | 11/2010 | Lim |
| 7,837,713 B2 | 11/2010 | Petersen |
| 7,837,732 B2 | 11/2010 | Zucherman et al. |
| D628,694 S | 12/2010 | Donnez |
| D629,896 S | 12/2010 | Horton |
| 7,846,210 B2 | 12/2010 | Perez-Cruet et al. |
| 7,850,733 B2 | 12/2010 | Baynham et al. |
| 7,850,735 B2 | 12/2010 | Eisermann et al. |
| 7,850,736 B2 | 12/2010 | Heinz |
| D631,156 S | 1/2011 | Halder et al. |
| 7,867,277 B1 | 1/2011 | Tohmeh |
| 7,897,164 B2 | 3/2011 | Scifert |
| 7,897,564 B2 | 3/2011 | Beals et al. |
| 7,905,840 B2 | 3/2011 | Pimenta et al. |
| 7,918,891 B1 | 4/2011 | Curran et al. |
| 7,927,361 B2 | 4/2011 | Oliver et al. |
| D637,721 S | 5/2011 | Horton |
| 7,935,124 B2 | 5/2011 | Frey et al. |
| 7,938,857 B2 | 5/2011 | Garcia-Bengochea et al. |
| 7,939,092 B2 | 5/2011 | McKay et al. |
| 7,964,208 B2 | 6/2011 | Spagnoli et al. |
| D641,872 S | 7/2011 | Solingen et al. |
| D641,873 S | 7/2011 | Solingen et al. |
| D641,874 S | 7/2011 | Solingen et al. |
| D642,268 S | 7/2011 | Qureshi |
| 7,985,256 B2 | 7/2011 | Grotz et al. |
| D643,921 S | 8/2011 | DÁVila |
| D647,202 S | 10/2011 | Scifert |
| 8,080,521 B2 | 12/2011 | Beals et al. |
| D655,414 S | 3/2012 | Cuschieri et al. |
| 8,148,326 B2 | 4/2012 | Beals et al. |
| D660,428 S | 5/2012 | Hohl |
| 8,198,238 B2 | 6/2012 | Beals et al. |
| 8,246,572 B2 | 8/2012 | Cantor et al. |
| 8,293,232 B2 | 10/2012 | Beals et al. |
| D692,133 S | 10/2013 | Steinwachs et al. |
| 2002/0049448 A1 | 4/2002 | Sand et al. |
| 2002/0058947 A1 | 5/2002 | Hochschuler et al. |
| 2003/0083748 A1 | 5/2003 | Lee et al. |
| 2003/0149482 A1 | 8/2003 | Michelson |
| 2003/0171812 A1 | 9/2003 | Grunberg et al. |
| 2003/0229358 A1 | 12/2003 | Errico et al. |
| 2004/0002713 A1 | 1/2004 | Olson et al. |
| 2004/0024466 A1 | 2/2004 | Heerklotz et al. |
| 2004/0073314 A1 | 4/2004 | White et al. |
| 2004/0087956 A1 | 5/2004 | Weikel et al. |
| 2004/0133217 A1 | 7/2004 | Watschke |
| 2004/0143330 A1 | 7/2004 | Sazy |
| 2004/0148027 A1 | 7/2004 | Errico et al. |
| 2004/0153158 A1 | 8/2004 | Errico et al. |
| 2004/0167532 A1* | 8/2004 | Olson et al. .................. 606/93 |
| 2004/0176853 A1 | 9/2004 | Sennett et al. |
| 2004/0215201 A1 | 10/2004 | Lieberman |
| 2004/0230211 A1 | 11/2004 | Moutafis et al. |
| 2005/0096601 A1 | 5/2005 | Doyle |
| 2005/0112091 A1 | 5/2005 | DiMauro et al. |
| 2005/0124993 A1 | 6/2005 | Chappuis |
| 2005/0124994 A1 | 6/2005 | Berger et al. |
| 2005/0149035 A1 | 7/2005 | Pimenta et al. |
| 2005/0149192 A1 | 7/2005 | Zucherman et al. |
| 2005/0159765 A1 | 7/2005 | Moutafis et al. |
| 2005/0165405 A1 | 7/2005 | Tsou |
| 2005/0216002 A1 | 9/2005 | Simonson |
| 2005/0216018 A1 | 9/2005 | Sennett |
| 2005/0251146 A1 | 11/2005 | Martz et al. |
| 2005/0251257 A1 | 11/2005 | Mitchell et al. |
| 2005/0261781 A1 | 11/2005 | Sennett et al. |
| 2005/0267443 A1 | 12/2005 | Staid et al. |
| 2005/0283150 A1 | 12/2005 | Moutafis et al. |
| 2006/0004367 A1 | 1/2006 | Alamin et al. |
| 2006/0015184 A1 | 1/2006 | Winterbottom et al. |
| 2006/0058585 A1 | 3/2006 | Oberlaender et al. |
| 2006/0058807 A1 | 3/2006 | Landry et al. |
| 2006/0100304 A1 | 5/2006 | Vresilovic et al. |
| 2006/0111779 A1 | 5/2006 | Petersen |
| 2006/0111780 A1 | 5/2006 | Petersen |
| 2006/0116770 A1 | 6/2006 | White et al. |
| 2006/0122597 A1 | 6/2006 | Jones et al. |
| 2006/0154366 A1 | 7/2006 | Brown et al. |
| 2006/0155170 A1 | 7/2006 | Hanson et al. |
| 2006/0167461 A1 | 7/2006 | Hawkins et al. |
| 2006/0190081 A1 | 8/2006 | Kraus |
| 2006/0229550 A1 | 10/2006 | Staid et al. |
| 2006/0247650 A1 | 11/2006 | Yerby et al. |
| 2006/0247791 A1 | 11/2006 | McKay et al. |
| 2006/0264808 A1 | 11/2006 | Staid et al. |
| 2006/0264964 A1 | 11/2006 | Scifert et al. |
| 2007/0003598 A1 | 1/2007 | Trieu |
| 2007/0043376 A1 | 2/2007 | Leatherbury et al. |
| 2007/0043442 A1 | 2/2007 | Abernathie |
| 2007/0067034 A1* | 3/2007 | Chirico et al. ............. 623/17.11 |
| 2007/0073110 A1 | 3/2007 | Larson et al. |
| 2007/0073294 A1 | 3/2007 | Chin et al. |
| 2007/0088007 A1 | 4/2007 | Ng |
| 2007/0093850 A1 | 4/2007 | Harris et al. |
| 2007/0123985 A1 | 5/2007 | Errico et al. |
| 2007/0172790 A1 | 7/2007 | Doucette, Jr. et al. |
| 2007/0185496 A1 | 8/2007 | Beckman et al. |
| 2007/0208423 A1 | 9/2007 | Messerli et al. |
| 2007/0213596 A1 | 9/2007 | Hamada |
| 2007/0213717 A1 | 9/2007 | Trieu |
| 2007/0213718 A1 | 9/2007 | Trieu |
| 2007/0213822 A1 | 9/2007 | Trieu |

(56) References Cited

U.S. PATENT DOCUMENTS

| | | |
|---|---|---|
| 2007/0213826 A1 | 9/2007 | Smith et al. |
| 2007/0225219 A1 | 9/2007 | Boden et al. |
| 2007/0225811 A1 | 9/2007 | Scifert et al. |
| 2007/0242869 A1 | 10/2007 | Luo et al. |
| 2007/0250166 A1 | 10/2007 | McKay |
| 2007/0264300 A1 | 11/2007 | Scifert et al. |
| 2007/0265632 A1 | 11/2007 | Scifert et al. |
| 2007/0270951 A1 | 11/2007 | Davis et al. |
| 2007/0276406 A1 | 11/2007 | Mahoney et al. |
| 2007/0288007 A1 | 12/2007 | Burkus et al. |
| 2007/0293948 A1 | 12/2007 | Bagga et al. |
| 2008/0003255 A1 | 1/2008 | Kerr et al. |
| 2008/0009929 A1 | 1/2008 | Harris et al. |
| 2008/0033440 A1 | 2/2008 | Moskowitz et al. |
| 2008/0058606 A1 | 3/2008 | Miles et al. |
| 2008/0071284 A1 | 3/2008 | Lechmann et al. |
| 2008/0086142 A1 | 4/2008 | Kohm et al. |
| 2008/0125856 A1 | 5/2008 | Perez-Cruet et al. |
| 2008/0147191 A1 | 6/2008 | Lopez et al. |
| 2008/0154375 A1 | 6/2008 | Serhan et al. |
| 2008/0154377 A1 | 6/2008 | Voellmicke |
| 2008/0154381 A1 | 6/2008 | Parrish |
| 2008/0172127 A1 | 7/2008 | Perez-Cruet et al. |
| 2008/0195058 A1 | 8/2008 | Moutafis et al. |
| 2008/0243126 A1 | 10/2008 | Gutierrez et al. |
| 2008/0249569 A1 | 10/2008 | Waugh et al. |
| 2008/0255564 A1 | 10/2008 | Michelson |
| 2008/0260598 A1 | 10/2008 | Gross et al. |
| 2008/0269904 A1 | 10/2008 | Voorhies |
| 2008/0288071 A1 | 11/2008 | Biyani et al. |
| 2008/0300598 A1 | 12/2008 | Barreiro et al. |
| 2009/0043312 A1 | 2/2009 | Koulisis |
| 2009/0076440 A1 | 3/2009 | Moutafis et al. |
| 2009/0076556 A1 | 3/2009 | McGarity et al. |
| 2009/0088765 A1 | 4/2009 | Butler et al. |
| 2009/0098184 A1 | 4/2009 | Govil et al. |
| 2009/0099660 A1 | 4/2009 | Scifert et al. |
| 2009/0105718 A1 | 4/2009 | Zhang et al. |
| 2009/0124860 A1 | 5/2009 | Miles et al. |
| 2009/0124980 A1 | 5/2009 | Chen |
| 2009/0125066 A1 | 5/2009 | Krau et al. |
| 2009/0142385 A1 | 6/2009 | Gross et al. |
| 2009/0187194 A1 | 7/2009 | Hamada |
| 2009/0192350 A1 | 7/2009 | Mejia |
| 2009/0192403 A1 | 7/2009 | Gharib et al. |
| 2009/0198245 A1 | 8/2009 | Phan |
| 2009/0198337 A1 | 8/2009 | Phan |
| 2009/0198338 A1 | 8/2009 | Phan |
| 2009/0198339 A1 | 8/2009 | Kleiner et al. |
| 2009/0203967 A1 | 8/2009 | Branch et al. |
| 2009/0204148 A1 | 8/2009 | Lenke |
| 2009/0204159 A1 | 8/2009 | Justis et al. |
| 2009/0204220 A1 | 8/2009 | Trieu |
| 2009/0222011 A1 | 9/2009 | Lehuec et al. |
| 2009/0228107 A1 | 9/2009 | Michelson |
| 2009/0246244 A1 | 10/2009 | McKay et al. |
| 2009/0248163 A1 | 10/2009 | King et al. |
| 2009/0259108 A1 | 10/2009 | Miles et al. |
| 2009/0264892 A1 | 10/2009 | Beyar et al. |
| 2009/0275995 A1 | 11/2009 | Truckai |
| 2009/0299477 A1 | 12/2009 | Clayton et al. |
| 2009/0306692 A1 | 12/2009 | Barrington et al. |
| 2010/0004752 A1 | 1/2010 | White et al. |
| 2010/0010367 A1 | 1/2010 | Foley et al. |
| 2010/0010524 A1 | 1/2010 | Barrington et al. |
| 2010/0016903 A1 | 1/2010 | Matityahu et al. |
| 2010/0016972 A1 | 1/2010 | Jansen et al. |
| 2010/0016973 A1 | 1/2010 | de Villiers et al. |
| 2010/0021518 A1 | 1/2010 | Scifert et al. |
| 2010/0030065 A1 | 2/2010 | Farr et al. |
| 2010/0036226 A9 | 2/2010 | Marino et al. |
| 2010/0036442 A1 | 2/2010 | Lauryssen et al. |
| 2010/0042221 A1 | 2/2010 | Boyd |
| 2010/0057208 A1 | 3/2010 | Dryer |
| 2010/0063516 A1 | 3/2010 | Parmer et al. |
| 2010/0063554 A1 | 3/2010 | Branch et al. |
| 2010/0076335 A1 | 3/2010 | Gharib et al. |
| 2010/0076445 A1 | 3/2010 | Pagano |
| 2010/0076446 A1 | 3/2010 | Gorek |
| 2010/0082036 A1 | 4/2010 | Reiley et al. |
| 2010/0087828 A1 | 4/2010 | Krueger et al. |
| 2010/0087875 A1 | 4/2010 | McGahan et al. |
| 2010/0100141 A1 | 4/2010 | de Villiers et al. |
| 2010/0105986 A1 | 4/2010 | Miles et al. |
| 2010/0105987 A1 | 4/2010 | Miles et al. |
| 2010/0112029 A1 | 5/2010 | Scifert |
| 2010/0121365 A1 | 5/2010 | O'Sullivan et al. |
| 2010/0121453 A1 | 5/2010 | Peterman |
| 2010/0125333 A1 | 5/2010 | Zdeblick et al. |
| 2010/0125338 A1 | 5/2010 | Fitz |
| 2010/0131020 A1 | 5/2010 | Heinz et al. |
| 2010/0137690 A1 | 6/2010 | Miles et al. |
| 2010/0137923 A1 | 6/2010 | Greenhalgh et al. |
| 2010/0145390 A1 | 6/2010 | McCarthy et al. |
| 2010/0145391 A1 | 6/2010 | Kleiner |
| 2010/0145452 A1 | 6/2010 | Blaylock et al. |
| 2010/0145461 A1 | 6/2010 | Landry et al. |
| 2010/0160923 A1 | 6/2010 | Sand et al. |
| 2010/0160982 A1 | 6/2010 | Justis et al. |
| 2010/0161062 A1 | 6/2010 | Foley et al. |
| 2010/0161074 A1 | 6/2010 | McKay |
| 2010/0168755 A1 | 7/2010 | Reiley et al. |
| 2010/0168862 A1 | 7/2010 | Edie et al. |
| 2010/0174326 A1 | 7/2010 | Selover et al. |
| 2010/0185286 A1 | 7/2010 | Allard |
| 2010/0185287 A1 | 7/2010 | Allard |
| 2010/0185288 A1 | 7/2010 | Carls |
| 2010/0191241 A1 | 7/2010 | McCormack et al. |
| 2010/0191334 A1 | 7/2010 | Keller |
| 2010/0191337 A1 | 7/2010 | Zamani et al. |
| 2010/0198140 A1 | 8/2010 | Lawson |
| 2010/0199483 A1 | 8/2010 | Justis et al. |
| 2010/0204798 A1 | 8/2010 | Gerbec et al. |
| 2010/0217398 A1 | 8/2010 | Keller |
| 2010/0222784 A1 | 9/2010 | Schwab et al. |
| 2010/0222824 A1 | 9/2010 | Simonson |
| 2010/0228294 A1 | 9/2010 | LeHuec et al. |
| 2010/0228351 A1 | 9/2010 | Ankney et al. |
| 2010/0234848 A1 | 9/2010 | Sutterlin et al. |
| 2010/0234957 A1 | 9/2010 | Zdeblick et al. |
| 2010/0249934 A1 | 9/2010 | Melkent |
| 2010/0256767 A1 | 10/2010 | Melkent |
| 2010/0256768 A1 | 10/2010 | Lim et al. |
| 2010/0262241 A1 | 10/2010 | Eisermann et al. |
| 2010/0262245 A1 | 10/2010 | Alfaro et al. |
| 2010/0266689 A1 | 10/2010 | Simonton et al. |
| 2010/0280622 A1 | 11/2010 | McKinley |
| 2010/0286778 A1 | 11/2010 | Eisermann et al. |
| 2010/0286784 A1 | 11/2010 | Curran et al. |
| 2010/0298938 A1 | 11/2010 | Humphreys et al. |
| 2010/0305575 A1 | 12/2010 | Wilkinson et al. |
| 2010/0312103 A1 | 12/2010 | Gorek et al. |
| 2010/0312290 A1 | 12/2010 | McKinley et al. |
| 2010/0312347 A1 | 12/2010 | Arramon et al. |
| 2010/0331847 A1 | 12/2010 | Wilkinson et al. |
| 2010/0331891 A1 | 12/2010 | Culbert et al. |
| 2011/0014587 A1 | 1/2011 | Spagnoli et al. |
| 2011/0015748 A1 | 1/2011 | Molz, IV |
| 2011/0020768 A1 | 1/2011 | Spagnoli et al. |
| 2011/0021427 A1 | 1/2011 | Amsden et al. |
| 2011/0028393 A1 | 2/2011 | Vickers et al. |
| 2011/0093005 A1 | 4/2011 | Strokosz et al. |
| 2011/0106162 A1 | 5/2011 | Ballard et al. |
| 2011/0144755 A1 | 6/2011 | Baynham et al. |
| 2011/0160777 A1 | 6/2011 | Spagnoli et al. |
| 2011/0184412 A1 | 7/2011 | Scifert et al. |
| 2011/0230970 A1 | 9/2011 | Lynn et al. |
| 2012/0022651 A1 | 1/2012 | Akyuz et al. |
| 2012/0035668 A1 | 2/2012 | Manninen et al. |
| 2012/0059477 A1 | 3/2012 | Kleiner |
| 2012/0065613 A1 | 3/2012 | Pepper et al. |
| 2012/0065687 A1 | 3/2012 | Ballard et al. |
| 2012/0078315 A1 | 3/2012 | Sweeney |

(56) References Cited

U.S. PATENT DOCUMENTS

| | | |
|---|---|---|
| 2012/0259335 A1 | 10/2012 | Scifert et al. |
| 2013/0073041 A1 | 3/2013 | Scifert et al. |
| 2013/0110169 A1 | 5/2013 | Hynes et al. |

OTHER PUBLICATIONS

U.S. Appl. No. 29/393,737, filed Jun. 8, 2011, Kleiner.
Ray, C., "Facet Joint Disorders and Back Pain," published on Spine-Health, Dec. 10, 2002, available at www.spine-health.com/conditions/arthritis/facet-joint-disorders-and-back-pain, 1 page.
Staehler, R., "Spine Surgery for a Cervical Herniated Disc," published on Spine-Health, Jun. 12, 2002, available at www.spine-health.com/conditions/herniated-disc/spine-surgery-a-cervical-herniated-disc, 2 pages.
Staehler, R., "Summary of Cervical Herniated Disc Treatment Options," published on Spine-Health, Jun. 12, 2002, available at www.spine-health.com/conditions/herniated-disc/summary-cervical-herniated-disc-treatment-options, 1 page.
Ullrich, P.F., "Anterior Cervical Spinal Fusion Surgery," published on Spine-Health, Oct. 7, 2005, available at www.spine-health.com/treatment/back-surgery/anterior-cervical-spinal-fusion-surgery, 2 pages.
Ullrich, P.F., "Cervical Spinal Instrumentation," published on Spine-Health, Oct. 7, 2005, available at www.spine-health.com/treatment/back-surgery/cervical-spinal-instrumentation, 2 pages.
Wascher, T.M., "Anterior cervical decompression and spine fusion procedure," published on Spine-Health, Aug. 29, 2001, available at www.spine-health.com/treatment/spinal-fusion/anterior-cervical-decompression-and-spine-fusion-procedure, 2 pages.
"BAK® /Proximity™(BP®) Cage", Zimmer Website, as early as Oct. 23, 2007, available at http://www.zimmer.com/z/ctl/op/global/action/1/id/7930/template/MP/prcat/M6/prod/y, printed on Jun. 8, 2009, 1 page.
"BAK® Vista® Radiolucent Interbody Fusion System", Zimmer Website, as early as Oct. 25, 2005, available at http://www.zimmerindia.com/z/ctl/op/global/action/1/id/7809/template/MP/prcat/M6/prod/y, printed on Jun. 8, 2009, pp. 1-2.
"Facet Joint Syndrome," The Cleveland Clinic Foundation, copyright 1995-2008, printed Nov. 19, 2008, available at http://my.clevelandclinic.org/disorders/facet_joint_syndrome/hic_facet_joint_syndrome.aspx, 2 pages.
"Screws, Cages or Both", Spine Universe Website, as early as Aug. 18, 2002, available at http://www.spineuniverse.com/displayarticle.php/article1363.html, printed on Jun. 8, 2009, pp. 1-13.
"University of Maryland Spine Program: A Patient's Guide to Anterior Lumbar Interbody Fusion with Intervertebral Cages", University of Maryland Medical Center website, as early as 2003, available at http://www.umm.edu/spinecenter/education/anterior_lumbar_interbody_fusion_with_intervertebral_cages.htm, printed on Jun. 8, 2009, pp. 1-4.
"Vertebral column," from Wikipedia, the free encyclopedia, printed May 19, 2009, retrieved from http://en.wikipedia.org/wiki/Vertebral_column, 6 pages.
"Zygapophysial joint," from Wikipedia, the free encyclopedia, printed May 19, 2009, retrieved from http://en.wikipedia.org/wiki/Zygapophysial_joint, 2 pages.
U.S. Appl. No. 13/367,295, filed Feb. 6, 2012, Kleiner.
U.S. Appl. No. 29/415,847, filed Mar. 14, 2012, Kleiner.
International Search Report for International (PCT) Patent Application No. PCT/US11/52278, mailed Jan. 18, 2012, 2 pages.
Written Opinion for International (PCT) Patent Application No. PCT/US11/52278, mailed Jan. 18, 2012, 5 pages.
International Search Report for International (PCT) Patent Application No. PCT/US2009/033488, mailed. Mar. 25, 2009, 2 pages.
Written Opinion for International (PCT) Patent Application No. PCT/US2009/033488, mailed. Mar. 25, 2009, 9 pages.
U.S. Appl. No. 13/473,366, filed May 16, 2012, Kleiner.
Official Action for U.S. Appl. No. 13/367,295, mailed May 2, 2012, 16 pages.
Official Action for U.S. Appl. No. 13/367,295, mailed Oct. 15, 2012, 14 pages.
Notice of Allowance for U.S. Appl. No. 14/088,148, mailed Feb. 3, 2014, 11 pages.
International Search Report and Written Opinion for International (PCT) Patent Application No. PCT/US2013/023992 mailed Apr. 26, 2013, 8 pages.
U.S. Appl. No. 13/754,042, filed Jan. 30, 2013, Kleiner.
U.S. Appl. No. 29/453,829, filed May 3, 2013, Kleiner.
U.S. Appl. No. 13/947,255, filed Jul. 22, 2013, Kleiner.
Ehrenberg, "The 3-D Printing Revolution," Science News, Mar. 9, 2013, pp. 20-25.
Notice of Allowance for U.S. Appl. No. 13/947,255, mailed Oct. 17, 2013, 16 pages.
International Preliminary Report on Patentability for International (PCT) Patent Application No. PCT/US11/52278, mailed Apr. 4, 2013, 7 pages.
Official Action for Australian Patent Application No. 2011305680, dated Jan. 31, 2014, 3 pages.
Notice of Allowance for Japanese Patent Application No. 2013-25835, mailed Mar. 28, 2014, 2 pages (includes English translation).
U.S. Appl. No. 29/427,387, filed Jul. 17, 2012, Kleiner.
U.S. Appl. No. 29/433,403, filed Sep. 28, 2012, Kleiner.
U.S. Appl. No. 13/632,956, filed Oct. 1, 2012, Kleiner.
U.S. Appl. No. 13/714,971, filed Dec. 14, 2012, Kleiner.
Notice of Acceptance for Australian Patent Application No. 2011305680, dated Aug. 27, 2014, 2 pages.
Official Action for Canadian Patent Application No. 2,811,018, dated Feb. 6, 2014, 2 pages.
Official Action for European Patent Application No. 11827323.4, dated Jul. 21, 2014, 3 pages.
International Preliminary Report on Patentability for International (PCT) Patent Application No. PCT/US2013/023992 mailed Aug. 14, 2014, 6 pages.
Official Action for Canadian Patent Application No. 153952, dated Apr. 15, 2014, 1 page.
Official Action for U.S. Appl. No. 13/367,295, mailed Jul. 14, 2014 9 pages.
Notice of Allowance for U.S. Appl. No. 29/453,829, mailed Oct. 8, 2014, 8 pages.

\* cited by examiner

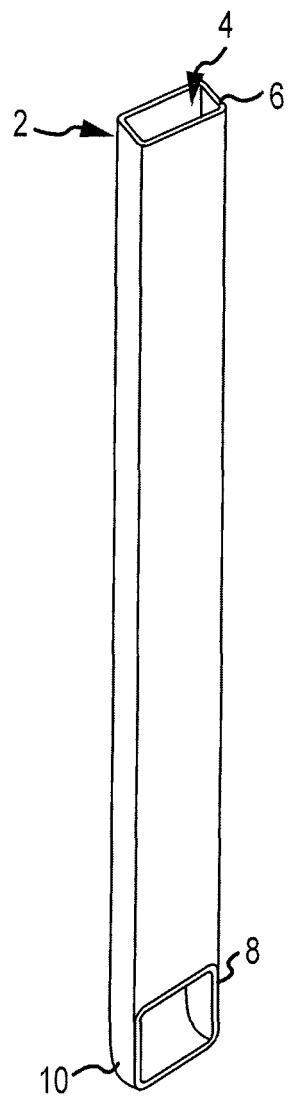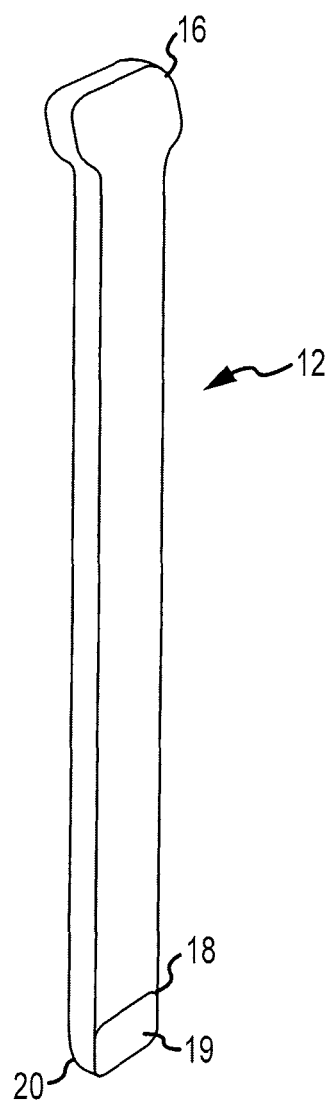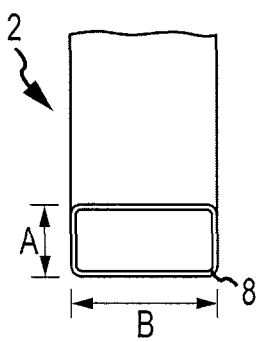
FIG.1A
FIG.1B
FIG.1C

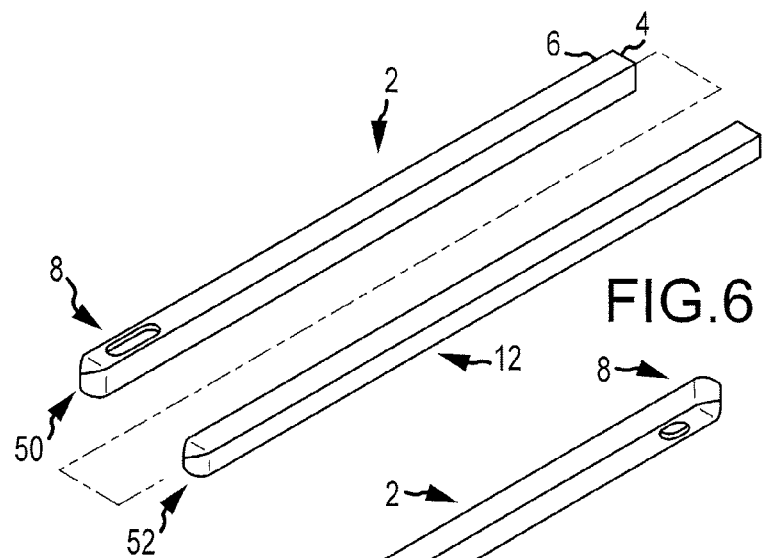
FIG. 6
FIG. 7
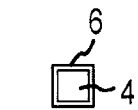
FIG. 8  FIG. 9
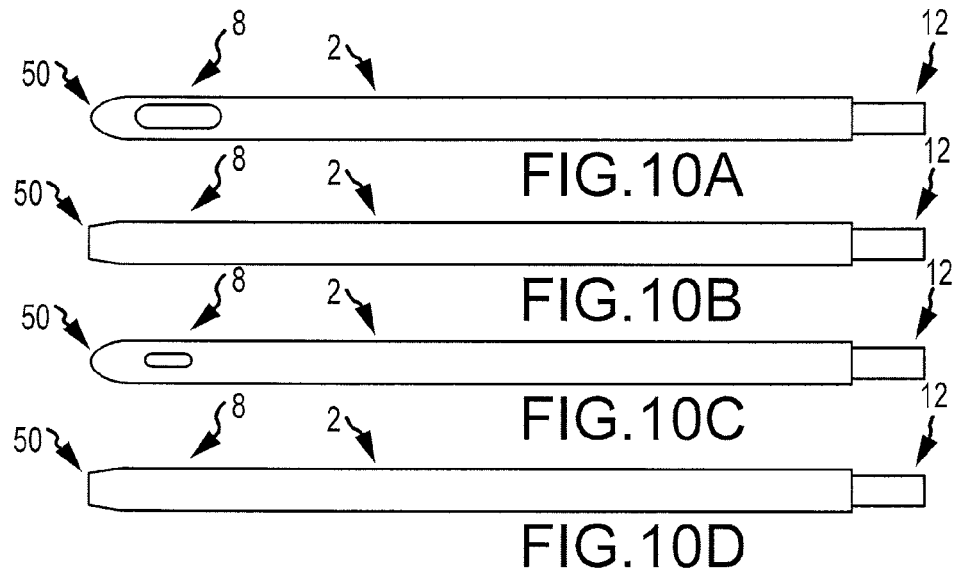
FIG. 10A
FIG. 10B
FIG. 10C
FIG. 10D

BONE GRAFT DELIVERY DEVICE AND METHOD OF USING THE SAME

CROSS REFERENCE TO RELATED APPLICATIONS

This application claims the benefit of U.S. Provisional Patent Application No. 61/243,664, filed on Sep. 18, 2009, the entire disclosure of which is incorporated by reference herein.

FIELD OF THE INVENTION

This disclosure relates to orthopedic surgery, and more specifically to an apparatus and method for inserting bone graft into a patient.

BACKGROUND OF THE INVENTION

Individuals who suffer degenerative disc disease, natural spine deformations, a herniated disc, spine injuries or other spine disorders may require surgery on the affected region to relieve the individual from pain and prevent further injury to the spine and nerves. Spinal surgery may involve removal of damaged joint tissue, insertion of a tissue implant and/or fixation of two or more adjacent vertebral bodies. The surgical procedure will vary depending on the nature and extent of the injury. For a general background on some of these procedures and the tools and apparatus used in certain procedures, see U.S. Prov. Pat. Appl. No. 61/120,260 filed on Dec. 5, 2008, the entire disclosure of which is incorporated by reference in its entirety. In addition, further background on procedures and tools and apparatus used in spinal procedures is found in U.S. patent application Ser. No. 12/632,720 filed on Dec. 7, 2009, the entire disclosure of which is incorporated by reference in its entirety.

Some disadvantages of traditional methods of spinal surgery include, for example, the pain associated with the procedure, the length of the procedure, the complexity of implements used to carry out the procedure, the prolonged hospitalization required to manage pain, the risk of infection due to the invasive nature of the procedure, and the possible requirement of a second procedure to harvest autograft bone from the iliac crest or other suitable site on the patient for generating the required quantity of cancellous and/or cortical bone.

A variety of semisolid bone graft materials are available on the market which ostensibly increase spinal fusion rates without the morbidity of autograft bone harvest. Each of the manufacturers espouses their product as the most advantageous for healing. These products all have similar handling characteristics and the literature reveals that they have similar healing prospects. They come in a syringe and it is up to the surgeon to apply the selected material to the target site. The most common site for application is to the disk space after it has been prepared to a bleeding bed and ready to accept a cage and/or the grafting material. This represents a long and narrow channel even in open procedures. The surgeon is left to his own devices as to how to get the graft from its container to the active site. The devices which have been used have included a "caulking gun" construct and a variety of barrel shaft with a plunger design.

The traditional devices for inserting bone graft impair the surgeon's visualization of the operative site, which can lead to imprecise insertion of bone graft and possible harm to the patient. The caulking gun and the collection of large barrel/plunger designs typically present components at the top of their structure which block the view of the surgical site. The surgeon must then resort to applying pressure to the surgical site to approximate the location of the device's delivery area. Such rough maneuvering can result in imprecise placement of bone graft, and in some cases, rupture of the surgical area by penetrating the annulus and entering the abdominal cavity. Also, in some surgical procedures, the devices for inserting bone graft material are applied within a cannula inserted or placed in the surgical area, further limiting the size and/or profile of the bone graft insertion device. When a cannula is involved, some traditional devices such as the large barrel/plunger designs and/or the chalking gun designs simply cannot be used as they cannot be inserted within the cannula.

Traditional devices for inserting bone graft deliver the bone graft material at the bottom of the delivery device along the device's longitudinal axis. Such a delivery method causes the bone grafting material to become impacted at the bottom of the delivery device, and promotes risk of rupture of the surgical area by penetrating the annulus and entering the abdominal cavity. Further, traditional devices that deliver bone graft material along their longitudinal axis may cause rupture of the surgical area or harm to the patient because of the ensuing pressure imparted by the ejected bone graft material from the longitudinal axis of the device.

Bone graft typically includes crushed bone (cancellous and cortical), or a combination of these (and/or other natural materials), and may further comprise synthetic biocompatible materials. Bone graft of this type is intended to stimulate growth of healthy bone. As used herein, "bone graft" shall mean materials made up entirely of natural materials, entirely of synthetic biocompatible materials, or any combination of these materials. Bone graft often is provided by the supplier in a gel or slurry form, as opposed to a dry or granule form. Many companies provide various forms of bone graft in varying degrees of liquidity and viscosity, which may cause problems in certain prior art delivery devices in both prepackaged or packaged by the surgeon embodiments. In addition, the method of delivery of bone graft to a particular location varies depending on the form of the bone graft utilized.

For example, in the case of slurry type bone graft, various dispensing devices have been developed having applicators designed to accommodate this type of bone graft. One such device is disclosed by U.S. Pat. No. 5,925,051 issued to Mikhail on Jul. 20, 1999 ("Mikhail"). Mikhail provides a caulking gun type dispenser for introducing bone graft in an enlarged bone (e.g. femoral) cavity. The device preferably includes a barrel pre-loaded with bone graft and a cannulated ejector positioned over a multi-section guide wire. This arrangement purports to accomplish both ejecting bone graft from the barrel and compacting the bone graft material while being guided on the guide wire. Mikhail, however, is designed solely for use with slurry-type bone graft, and does not accommodate bone graft in granule form, which often varies in size among granules and does not have the same "flow" or viscosity characteristics as slurry-type bone graft. Thus, the applicator of Mikhail is insufficient for introducing most bone graft to a surgical site in a patient.

U.S. Pat. No. 6,019,765 issued to Thornhill et al. on Feb. 1, 2000 ("Thornhill") also teaches a bone graft delivery device. The bone graft device applicator of Thornhill is used to apply bone graft to an artificial joint without having to remove a previously implanted prosthesis component. The applicator device includes a hollow tube with an actuation mechanism for discharging the bone graft from the device via a nozzle coupled to a distal end of the tube. The bone graft delivery device of Thornhill may include various components for loading the device with the bone graft, and may further include a plurality of nozzles each having a geometry suited for a particular application. Like Mikhail, the Thornhill delivery device is designed for use with bone slurry, and requires much custom instrumentation and different sized parts to achieve success in many bone graft delivery applications, which in turn increases the time to assemble and use the delivery device and may create further problems during the surgical operation.

U.S. Pat. No. 5,697,932 issued to Smith et al. on Dec. 16, 1997 ("Smith") discloses yet another bone graft delivery system and method. In Smith, a hollow tube of pre-loaded bone graft and a plunger are used to facilitate delivery of the bone graft to a bone graft receiving area. A positioning structure is provided on the plunger to maintain the plunger in a desirable position with respect to the hollow tube. Adjunct positioning means may also be provided to ensure that the plunger remains in the desirable position during the packing of bone graft into the bone graft receiving area. Like the devices of Thornhill and Mikhail, the device disclosed by Smith is clearly designed solely for slurry type bone graft, and does not provide an effective opening for receiving the desired amount of bone graft. Furthermore, the hollow tube shown by Smith is narrow and does not have a footing or other apparatus associated with the delivery device for preventing the device from penetrating, for example, the abdominal region of a patient, which may occur during tamping or packing of the bone graft. This in turn may cause serious injury to a patient if not controlled, and for these reasons the device of Smith is also insufficient for delivery of bone graft to a surgical site.

The prior art bone graft delivery devices listed above must come pre-loaded with bone graft, or alternatively require constant loading (where permissible) in order to constantly have the desired supply of bone graft available. Moreover, these devices cannot handle particulate bone graft of varying or irregular particulate size. These problems can be a great inconvenience, and make these prior art devices unsuitable in many procedures.

SUMMARY OF THE INVENTION

Certain embodiments of the present disclosure relate to a bone graft delivery device and method for using the same. The device is comprised generally of a tubular member and a plunger for expelling bone graft from the tubular member and into a bone graft receiving area preferably at a surgical site in a human patient. Other embodiments and alternatives to this device are described in greater detail below.

By way of providing additional background, context, and to further satisfy the written description requirements of 35 U.S.C. §112, the following references are incorporated by reference in their entireties for the express purpose of explaining the nature of the surgical procedures in which bone graft is used and to further describe the various tools and other apparatus commonly associated therewith: U.S. Pat. No. 6,309,395 to Smith et al.; U.S. Pat. No. 6,142,998 to Smith et al.; U.S. Pat. No. 7,014,640 to Kemppanien et al.; U.S. Pat. No. 7,406,775 to Funk, et al.; U.S. Pat. No. 7,387,643 to Michelson; U.S. Pat. No. 7,341,590 to Ferree; U.S. Pat. No. 7,288,093 to Michelson; U.S. Pat. No. 7,207,992 to Ritland; U.S. Pat. No. 7,077,864 to Byrd III, et al.; U.S. Pat. No. 7,025,769 to Ferree; U.S. Pat. No. 6,719,795 to Cornwall, et al.; U.S. Pat. No. 6,364,880 to Michelson; U.S. Pat. No. 6,328,738 to Suddaby; U.S. Pat. No. 6,290,724 to Marino; U.S. Pat. No. 6,113,602 to Sand; U.S. Pat. No. 6,030,401 to Marino; U.S. Pat. No. 5,865,846 to Bryan, et al.; U.S. Pat. No. 5,569,246 to Ojima, et al.; U.S. Pat. No. 5,527,312 to Ray; and U.S. Pat. Appl. No. 2008/0255564 to Michelson.

According to varying embodiments described herein, the present invention is directed to the delivery of bone graft materials to any area of the body, and in particular to the intervetebral joints of the spine, for achieving bone graft fusion. However, the invention may be used in the repair of a bone joint or in connection with the implantation of prosthetic devices in the body, including, by way of example but not limitation, the hip, knee and a variety of spinal joints. Also, the present invention may be used in primary surgery, in which a bone graft is being supplied to promote new bone growth or to reconstruct a joint for the first time, as well as in revision surgery, in which a follow-up procedure is being performed in an area that has previously been subject to one or more surgeries. Further, the invention may be used in any application where material is to be delivered with precision to a confined area where access is restricted, to include surgical procedures, repair of installed or uninstalled mechanical or electrical devices, and arming or disarming of explosive devices.

According to various embodiments of the present disclosure, one aspect of the invention is to provide a graft delivery device that comprises a tubular member, which is substantially hollow or contains at least one inner lumen and that has a generally rectangular cross-sectional shape. This generally rectangular cross-sectional shape offers a larger amount of surface area through which bone graft material may be inserted and ejected from the hollow tubular member. Furthermore, this generally rectangular shape is more congruent with the size or shape of the annulotomy of most disc spaces, which frequently are accessed by a bone graft delivery device for delivery of bone graft. However, as one skilled in the art would appreciate, the tool cross-section need not be limited to a generally rectangular shape. For example, cross-sections of an oval shape or those with at least one defined angle to include obtruse, acute, and right angles can provide a shape in some situations that is more congruent with the size or shape of the annulotomy of a particular disc space. A substantially round shape may also be employed that provides the surgeon with an indication of directional orientation.

According to various embodiments of the present disclosure, it is another aspect that the hollow tubular member further comprise at least one opening on a lateral face or surface of the hollow tubular member, at one distal end, for ejecting bone graft material into a bone graft receiving area, such as a disc space, such that the bone graft material is ejected from the hollow tubular member in a manner that does not interfere with the area of the patient for receiving any additional implant, such as a structural cage implant. In addition, the graft material is dispersed into the area of the debrided disc space rather than in the path of the cage. Thus, the device may be used in a method for depositing bone graft material into a debrided disc space without substantially delivering bone graft material into the path of a structural cage implant. The method comprises precisely inserting the bone graft delivery device, in one or more of the embodiments contained herein, into the surgical area that may contain one or more additional implants, such as a structural cage implant. The bone graft delivery device is then filled with bone graft material in its one or more substantially hollow tubes, the one or more plunger's are inserted into the one or more hollow tubes, and the one or more plunger are pushed into the one or more hollow tubes, guided precisely as enabled by the minimal profile of the device, therein controllably depositing the bone graft material into the surgical area without depositing bone graft material into the path of a structural cage implant or other implant.

In a preferred embodiment, the bone graft delivery device comprises a hollow tube or contains at least one inner lumen constructed to receive bone graft, and a plunger adapted for insertion at least partially within the hollow tube and preferably through the full extent of the hollow tube. The plunger of some embodiments is generally of the same geometric configuration as the hollow interior potion of the hollow tube so that the plunger, once fully inserted in to the hollow tube, is substantially congruent with the hollow interior portion of the hollow tube, e.g. both the plunger and the hollow tube are substantially the same shape and/or class. The plunger preferably extends about the same length as the hollow tube, and further comprises an end portion, e.g. at least one knob or handle for grasping and manipulation by a user, or in robotic or automated or semi-automated control or surgeries, by a machine.

Also according to a preferred embodiment, the hollow interior portion of the hollow tube further comprises a sloped or curved surface at a second end (e.g. positioned near a place for deposit of bone graft material) adjacent and opposite a lateral window or opening in a lateral face of the hollow tube. As the interior of the hollow tube comprises a sloped or curved surface at its second end, the plunger also comprises a sloped or curved surface at a second end of the plunger. The plunger terminates opposite the curved surface at its second end with a laterally faced surface, which corresponds to the lateral window or opening at the second end of the hollow tube. Thus, in cooperation, the plunger may be inserted into the opening of the hollow tube, and extended the entire length of the hollow tube, at least to a point where the laterally faced surface of plunger is in communication with the lateral window or opening at the second end of the hollow tube. This configuration permits a user to eject substantially all of the bone graft material that is placed into the hollow tube in a lateral direction at the bone graft receiving area during a surgical procedure.

Another embodiment for the bone graft insertion device comprises a hollow tube constructed to receive bone graft, where the hollow tube has a proximal and distal end, a plunger adapted for insertion at least partially within the hollow tube at the proximal end of the hollow tube, whereby the plunger is constructed and arranged with respect to the hollow tube so as to prevent rotation of the plunger during insertion into said hollow tube, whereby the plunger has a distal end that is contoured to an interior surface of the distal end of the hollow tube such that the contoured distal end of the plunger is nearly congruent with the interior surface of the distal end of the hollow tube for removing substantially all of the bone graft received by the hollow tube and whereby the bone graft is delivered to the graft receiving area. Still another embodiment provides a rifling structure in the hollow tube interior that facilitates rotational movement of the plunder along a lengthwise axis of the hollow tube, therein delivering a substantially steady pressure and/or rate of delivery of the bone graft material as the plunger descends the hollow tube when the plunger is forced through the hollow tube. The rifling or screw-like movement may also translate to a predetermined delivery of material per full rotation, e.g. each 360 degree rotation of the plunger equates to 5 cc of bone graft material delivered to the bone graft site.

Another aspect of the present invention includes providing a hollow tube and plunger assembly, in which the hollow tube and/or the plunger assembly are disposable. The tube may also be at least portions of biocompatible material which can stay in the canal without impairing the final implantation. Alternatively, it may thus be a material that is resorbable, such as a resorbable polymer, in the canal after implantation, so as not to interfere with the growth of the bone or stability of the implant.

A further embodiment of the invention provides pre-packaged inserts for loading into the hollow tube element, or if there are a plurality of hollow tube elements, into one or more of the hollow tube elements. The pre-packaged inserts may be of varying lengths, and/or layered of differing materials or components, to include the patient's own bone graft matter.

Another embodiment of the present invention provides a bone graft delivery system, by which a hollow tube and/or a hollow tube/plunger assembly can be prepared prior to opening a patient, thus minimizing the overall impact of the grafting aspect of a surgical implantation or other procedure. Moreover, the hollow tube may be made to be stored with bone graft in it for a period of time, whether the tube is made of plastic, metal or any other material. Depending upon the surgical application, it may be desirable to only partially fill the tube for storage, so that a plunger can be at least partially inserted at the time of a surgery.

A further embodiment of the present invention provides a bone graft insertion apparatus comprising a hollow tube constructed to receive bone graft, the hollow tube having a proximal and distal end whereby the hollow tube contains least one opening on a surface of the distal end of the hollow tube. The at least one opening is preferably positioned other than completely along the axial or longitudinal axis of the device. The number and size and shape of such openings can vary but are preferably adapted to deliver bone graft material in a direction substantially transverse to the axial extent of the substantially hollow tube. In one embodiment, two or more apertures are provided. In certain embodiments, apertures are on the same side of the hollow tube, where in others, apertures are on different sides (e.g. opposing sides) of a hollow tube. A plunger, adapted for insertion at least partially within the hollow tube, is constructed and arranged with respect to the hollow tube so as to present at least one substantially flat contour, whereby the plunger has a distal end that is contoured to an interior surface of the distal end of the hollow tube such that the contoured distal end of the plunger is nearly congruent with the interior surface of the distal end of the hollow tube. This facilitates removing substantially all of the bone graft received by the hollow tube whereby the bone graft is delivered to the graft receiving area. It is important to remove substantially all of the bone graft material as it is expensive and/or difficult to obtain.

In another embodiment of the present disclosure the distal end of the plunger is flexible to allow, for example, the user to maneuver the distal end and thereby any bone graft material in the hollow tube to the implantation site. One skilled in the art will appreciate that the flexible aspect of certain embodiments can be both passive and active in nature. Active flexibility and manipulation in the distal end of the plunger may incorporate, for example, the manipulative capabilities of an endoscope, including components for manipulation such as guidewires along the longitudinal axis of the shaft of the plunger.

In another embodiment of the invention, the distal end and the proximal end of the hollow tube are in communication via a conduit to enable electrical, hydraulic, pneumatic, or mechanical transmission, the later such as a wire. Such hydraulic communication allows, for example, a medical or other liquid to be delivered or extracted from the surgical area. Such mechanical communication allows, for example, the distal end to be maneuvered precisely.

In another embodiment of the present disclosure, the hollow tube and/or plunger may be curved and/or may have an angular aspect, in addition to the sloped or curved surface at a second end of the hollow tube/plunger. This shape may, for example, aid the surgeon in more comfortably introducing the delivery device to the implant site, be shaped to better accommodate implantation sites on right or left sides of the body, or be shaped to better accommodate right or left-handed surgeons. One having skill in the art will appreciate that the delivery device may have multiple angles and curved aspects which enable aspects of embodiments of the present disclosure or aid in ergonomics.

In one embodiment of the present disclosure, the device further comprises a footing or shelf at the distal end of the tubular device that is nearest the operating site for preventing or mitigating risk of injury to the patient during surgery. According to this embodiment, the footing may be flexible, semi-flexible, semi-rigid or rigid. The footing serves to protect the anatomy of the patient from being penetrated by the hollow tube of the bone graft delivery device when the plunger is being inserted or during tamping of the hollow tube or the plunger by the surgeon, which may occur during the surgical procedure for a variety of reasons. In certain embodiments, the distal tip region of the hollow tube comprises a softer, maliable and/or less rigid material than the remainder of the hollow tube.

It is yet another aspect of the present disclosure to provide a bone graft delivery device that contains one or more detachable elements for use in an operation where bone graft material must be inserted into the bone graft delivery device and ejected to a bone graft receiving area. According to various embodiments, these detachable devices may include a detachable funnel for gathering and inserting bone graft material at a graspable end of the bone graft delivery device. The present disclosure may also comprise a plunger that has a detachable handle, which may be selectively removed to avoid blocking the surgeon's view of the operating site. The bone graft delivery device may further comprise a detachable footing or shelf at one distal end of the hollow tubular member. In one embodiment this footing or shelf is selectively positionable about various points along the hollow tube. For example, a distal portion of the hollow tube has a rotatable portion that can be positioned to deliver bone graft material to areas of a disc space in a manner such that a surgeon has angular directional control as to where bone graft material is directed. Other detachable elements are also contemplated with the present invention, such as a funnel at the proximal end of the hollow tube, or exterior or interior guide wires attached to the hollow tube, or a camera which is positioned near the delivery site of the bone graft material.

Thus, according to various embodiments of the present disclosure, a method of introducing bone graft material to a desired operating site ("bone graft receiving area") is provided by use of a hollow tubular member comprising a generally rectangular cross-sectional area, whereby the desired operating area is capable of receiving at least one plunger. The one or more plunger having at least one distal end which is designed to accommodate ejecting bone graft or other material to be inserted into the joint space or between intervertebral members in a generally lateral direction, as opposed to a generally longitudinal direction (in relation to the direction of the primary axis of the device).

One skilled in the art will appreciate that the distal end of the tubular device need not be limited to those specific embodiments described above. Other forms, shapes or designs that enable the foregoing aspects of the present invention are hereby incorporated into this disclosure. Forms, shapes and designs that relate to the provision of an end of a tubular device to perform lateral introduction of bone or bone substitute to an operating site are considered to be within the scope of the present disclosure.

One aspect of the present invention provides a bone graft delivery system for delivering bone graft, in a partially formed, fully formed or unformed condition to a bone graft receiving area in a body.

In yet another embodiment the hollow tube of the bone graft delivery device may further comprise a funnel on the graspable end of the hollow tube, which may be selectively positioned about the graspable end of the hollow tube, for facilitating insertion of new or additional bone graft into the hollow tube. The funnel may take on a variety of shapes and sizes, depending on the nature of the bone graft material being inserted in the hollow tube.

One embodiment of the substantially hollow tube provides that the hollow tube is telescoping, thereby allowing its length to be adapted to the particular desires of the surgeon and/or the surgical area. In this embodiment, the plunger may also be telescoping to substantially conform to the configuration and/or size and/or shape of the substantially hollow tube.

In another embodiment, the size and/or shape of the one or more hollow tubes of the device are sized to fit, and/or not substantially obscure access to the aperture of, the cannula or cannulas that the device is fitted through for delivery of bone graft material to the operating site. In this embodiment, the device's one or more pair of hollow tubes and plungers do not substantially impair access to the operating site nor the surgeon's view of the operating site One of ordinary skill in the art will appreciate that embodiments of the present disclosure may have various sizes. The sizes of the various elements of embodiments of the present disclosure may be sized based on various factors including, for example, the anatomy of the implant patient, the person or other device operating the apparatus, the implant location, physical features of the implant including, for example, with, length and thickness, and the size of operating site or the size of the surgical tools being used with the device.

One or ordinary skill in the art will appreciate that embodiments of the present disclosure may be constructed of materials known to provide, or predictably manufactured to provide the various aspects of the present disclosure. These materials may include, for example, stainless steel, titanium alloy, aluminum alloy, chromium alloy, and other metals or metal alloys. These materials may also include, for example, PEEK, carbon fiber, ABS plastic, polyurethane, rubber, latex, synthetic rubber, and other fiber-encased resinous materials, synthetic materials, polymers, and natural materials. The plunger element could be flexible, semi-rigid, or rigid and made of materials such as stainless steel, titanium alloy, aluminum alloy, chromium alloy, and other metals or metal alloys. Similarly, the tubular element could be flexible, semi-rigid, or rigid and made of materials such as stainless steel, titanium alloy, aluminum alloy, chromium alloy, and other metals or metal alloys. In certain embodiments, the plunger and hollow tube are composed of plastic and are intended for one use only and then discarded. In another embodiment, some or all elements of the device, or portions of some or all of the elements, are luminescent. Also, in another embodiment, some or all elements of the device, or portions of some or all of the elements, include lighting elements. In another embodiment, the hollow tube and/or plunger are made of a substantially transparent material and/or are rigidly opaque.

One of ordinary skill in the art will appreciate that embodiments of the present disclosure may be controlled by means other than manual manipulation. Embodiments of the present disclosure may be designed and shaped such that the apparatus may be controlled, for example, remotely by an operator, remotely by an operator through a computer controller, by an operator using proportioning devices, programmatically by a computer controller, by servo-controlled mechanisms, by hydraulically-driven mechanisms, by pneumatically-driven mechanisms or by piezoelectric actuators.

Embodiments of the present disclosure present several advantages over the prior art including, for example, the speed of the procedure, the minimally invasive aspect of the procedure, the ability to introduce the implant material to the implant site with minimal risk and damage to the surrounding tissue, the lower risk of infection, more optimally placed implant material, a more stable delivery device which is designed to reduce the likelihood of the implant material becoming dislodged prior to fixation, and fewer tools in a surgical site due to the integration of several components required to provide bone graft to a bone graft receiving area. Further, the lower profile of the device allows improved viewing of the area intended for receipt of bone graft material, and use of a reduced set and size of elements therein provided a less expensive device. Also, the device disclosed provides that substantially all of the bone graft material may be ejected from the device and delivered to the surgical site, rather than wasted as unretrievable matter remaining inside the device. The ability to remove substantially all of the bone graft material is of significant benefit because the bone graft material is expensive and/or hard to obtain.

This Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention, and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. However, the Detailed Description of the Invention, the drawing figures, and the exemplary claim set forth herein, taken in conjunction with this Summary of the Invention, define the invention.

BRIEF DESCRIPTION OF THE DRAWINGS

The accompanying drawings, which are incorporated in and constitute a part of the specification, illustrate embodiments of the disclosure and together with the general description of the disclosure given above and the detailed description of the drawings given below, serve to explain the principles of the disclosures.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

FIG. 1A is a perspective view of the device for delivering bone graft;

FIG. 1B is a perspective view of the plunger of the device;

FIG. 1C is a cross sectional view of a portion of the device shown in FIG. 1A;

FIG. 6 is a perspective view of one embodiment of the device, showing the relationship between the tubular and plunger portions where the tubular portion includes two lateral facing openings at the distal end of the tubular portion and a wedge-shaped distal end of the tubular member;

FIG. 7 is a another perspective view of the tubular portion of the device of FIG. 6 showing the second of two lateral openings at the distal end of the tubular portion and a wedge-shaped distal end of the tubular member;

FIG. 8 is an elevation view of the of the distal end of the tubular portion of the device;

FIG. 9 is an elevation view of the proximal end of the tubular device;

FIG. 10A-D are sequential elevation views of the device with the plunger portion fully inserted into the tubular portion;

DETAILED DESCRIPTION

Figure 2:
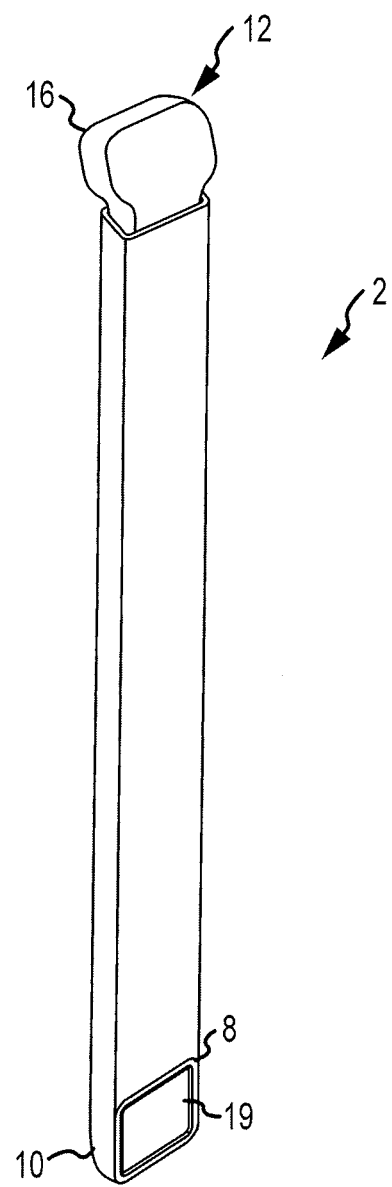
FIG. 2 is another perspective view of the device of FIGS. 1A-C, showing the relationship between the tubular and plunger portions of the device of FIG. 1.

The present invention relates to a device and method for delivery of bone graft material to any portion of a patient which requires bone graft material. Thus, for example, the foregoing description of the various embodiments contemplates delivery to, for example, a window cut in a bone, where access to such window for bone grafting is difficult to obtain because of orientation of such window, presence of muscle tissue, risk of injury or infection, etc. The bone graft delivery device is formed such that the one or more hollow tubes and/or plungers may be helpful in selectively and controllably placing bone graft material in or adjacent to such window. The bone graft delivery device is formed to allow delivery of bone graft material in a direction other than solely along the longitudinal axis of the device, and in some embodiments transverse to the primary axis used by the surgeon or operator of the device when inserting the device into a cannula or other conduit to access the surgical site. This same concept applies to other areas of a patient, whether or not a window has been cut in a bone, for example in a vertebral disc space, and may be used whether this is a first surgery to the area or a follow-up surgery. The present invention also contemplates the delivery of bone graft material with or without the use of a plunger, and with or without the use of various other tools described in greater detail herein.

Referring now to FIGS. 1-10, several embodiments of the present invention are shown.

In regard to FIG. 1A, a bone graft delivery device portion is shown, which is comprised of a hollow tubular member or hollow tube or contains at least one inner lumen 2, which has a first proximate end 6 (which is referred to elsewhere in this specification as the "graspable end" of hollow tube 2), and a second distal end 8, with a general hollow structure therebetween. Thus, as shown in FIG. 1, the hollow tube 2 allows bone graft material to be inserted into the opening 4 at the graspable end 6 of the hollow tube 2, and ultimately exited from the hollow tube 2 through the second end 8. According to a preferred embodiment, the hollow tube 2 also comprises at least one sloped or curved surface 10 at or near the second end 8 of the hollow tube 2. Although a generally rectangular cross-section is depicted, the cross-section need not be limited to a generally rectangular shape. For example, cross-sections of an oval shape or those with at least one defined angle to include obtruse, acute, and right angles can provide a shape in some situations that is more congruent with the size or shape of the annulotomy of a particular disc space.

Referring now in detail to FIG. 1B, a plunger 12 is shown for use with the hollow tube 2 of FIG. 1A. The plunger 12 is generally of the same geometry as the hollow potion of the hollow tube 2, extending at least the same length of hollow tube 2. The plunger 12 may includes, as depicted in FIG. 1B at least one knob or handle 16 for grasping by a user of the plunger 12. As with the interior of the hollow tube 2 at its second end 8, the plunger 12 also comprises at least one sloped or curved surface 20 at or adjacent to a second end 18 of the plunger 12. The plunger 12 terminates in a generally flat, horizontal surface 19, which corresponds to the opening at the second end 8 of the hollow tube 2 shown in FIG. 1A. Thus, in cooperation, the plunger 12 may be inserted into the opening 4 of the hollow tube 2 shown in FIG. 1A, and extended the entire length of the hollow tube 2, at least to a point where the horizontal surface 19 of plunger 12 is in communication with the second end 8 of the hollow tube 2. This configuration permits a user to eject substantially all of the bone graft material that is placed into the hollow tube 2 during a surgical procedure. One skilled in the art will appreciate that the plunger need not terminate in a generally flat, horizontal surface to effect the substantial removal of all of the bone graft material placed into the hollow tube; more specifically, any shape that allows conformance between the internal contour of the distal end of the hollow tube and the distal end of the plunger will effect the substantial removal of the bone graft material. Further details about the relationship are described below in regard to FIG. 2.

In the embodiment, of FIG. 1A-C, a contoured leading edge is provided on the plunger to correspond with the internal contour of distal end of the hollow tube of the delivery device. This contoured plunger serves several purposes: First, it maintains the plunger in a desirable rotational position with respect to the hollow tube (i.e., prevent the plunger from inadvertently or intentionally being manipulated to rotate about the longitudinal axis of the hollow tube); Second, it ensure that when the plunger is fully inserted, the plunger removes substantially all of the bone graft material from the hollow tube. Also, the contoured plunger, corresponding to the contoured tubular member, allows immediate identification of the orientation of the device, and more specifically the direction of eject of the bone graft material into the surgical area. Alternative positioning means may also be provided to ensure that the plunger remains in the desirable position during delivery of bone graft into the hollow tube, for example by a machined bevel or edge on the outer surface of the plunger, and a corresponding groove in the interior surface of the hollow tube, which must be aligned when inserting the plunger in the hollow tube.

Referring now to FIG. 1C, an elevation view of the hollow tube 2 shown in FIG. 1A is shown in detail. The second end 8 of the hollow tube 2 has an opening with a height A and width B according to the needs of the surgeon, the location of the bone graft receiving area, the nature of the surgical operation to be performed, and the quantity and type of bone graft that is being inserted in (and ultimately ejected from) this bone graft delivery device. According to a preferred embodiment, the height A of the opening at the second end 8 of the hollow tube 2 is in the range of 4 mm to 9 mm, and in a most preferred embodiment is about 7 mm. According to a preferred embodiment, the width B of the opening at the second end 8 of the hollow tube 2 is in the range of 7 mm to 14 mm, and in a most preferred embodiment is about 10 mm.

Referring to FIGS. 1A-C, it is to be understood that although these particular drawings reflect an embodiment where the second end 8 of the hollow tube 2, and the second end 18 of the plunger 12 comprise a curved or sloped surface which extends at least a certain distance laterally away from the generally longitudinal axis of the hollow tube 2/plunger 12, that in other embodiments, the second end 8 of the hollow tube 2 (and thereby, the second end 18 of the plunger 12) do not extend a lateral distance away, but rather terminate along the longitudinal wall of the hollow tube 2. In this embodiment, the hollow tube 2 may have a second end 8 which has an opening that is carved out of the side of the wall of the hollow tube 2, such that it appears as a window in the tubular body of hollow tube 2. According to this embodiment, the horizontal face 19 of the plunger 12 would also be a face on the outer surface of plunger 12, without extending any lateral distance away from the body of plunger 12. According to this embodiment, the plunger 12 would still retain the curved or sloped surface at the opposite end of the horizontal face 19 (referred to in FIG. 1B as 20) and similarly the hollow tube 2 would still comprise a sloped or curved surface 10 opposite the opening at second end 8. It is to be expressly understood that other variations which deviate from the drawing FIGS. 1A-C are also contemplated with the present invention, so long as that the opening at the second end 8 of hollow tube 2 is oriented to permit bone graft to be exited from the hollow tube 2 in a generally lateral direction (in relation to the longitudinal direction of the axis of the hollow tube 2).

According to another embodiment, the plunger 12 shown in FIG. 1B may further comprise a secondary handle (not shown in FIG. 1B), which includes an opening about at least one end of secondary handle such that it is permitted to couple with handle 16 of plunger 12. In this fashion, the secondary handle may be larger, contain one or more rings or apertures for placing a users hand and/or fingers, or may simply be of a more ergonomic design, for accommodating use of the plunger 12 during a surgical operation. The secondary handle, according to this embodiment, is selectively removable, which permits a surgeon to use the secondary handle for inserting the plunger 12, and then at a later point remove the secondary handle, for instance, to improve visibility through the incision or through the hollow tube 2, and/or to determine whether substantially all of the bone graft material has been ejected from the hollow tube 2.

Referring now in detail to FIG. 2, the plunger 12 is shown inserted into the hollow tube 2, such that the horizontal face 19 is substantially planar with the opening at the second end 8 of the hollow tube 2. As described above, the geometry of plunger 12 is such that it fits snuggly or tightly in the interior of the hollow tube 2. This configuration is such that the sloped or curved surface 10 of the hollow tube 2 is substantially congruent to the sloped or curved surface 20 (not shown in FIG. 2), thereby allowing the plunger to be inserted into the hollow tube 2 and allowing substantially all of bone graft material which is placed into the hollow tube 2 to be ejected by the user.

Figure 3:
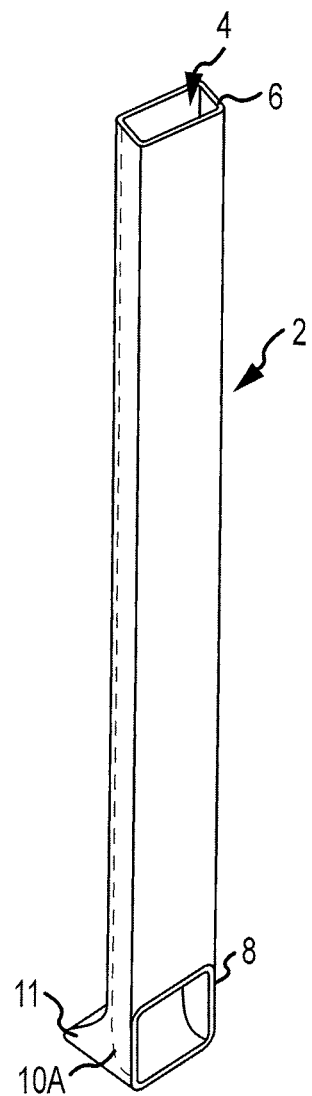
FIG. 3 is a perspective view of the device according to one alternative embodiment where the tubular portion includes a foot section and where the plunger portion has been fully inserted into the tubular portion.

Referring now in detail to FIG. 3, an alternate embodiment of the present invention is shown. According to this embodiment, the hollow tube 2 comprises a footing 11 at the second end 8 of the hollow tube 2. This footing 11 extends in a lateral direction, opposite the direction of the opening at the second end 8 of the hollow tube 2. The purpose of this footing 11 is to prevent injury to the annulus of a patient, or other sensitive anatomy adjacent the bone graft receiving area. This footing 11 is helpful when a surgeon or other user of the bone graft delivery device is using the plunger 12 to drive bone graft through the hollow tube 2, or using another tool, such as a tamp, mallet, or other driving or impacting device to strike the plunger 12 and/or hollow tube 2 during the surgical procedure. Without the footing 11, the hollow tube 2 would have a generally angular second end 8, which may cause damage to the patient during these types of procedures. Thus, the footing 11 prevents the second end 8 of the hollow tube 2 from penetrating the annulus or other sensitive anatomy of the patient.

According to this embodiment, the footing 11 may also operate to ensure a fixed position of the second end 8 of the hollow tube 2 in the surgical site. This in turn allows a user to ensure that bone graft ejecting the second end 8 of the hollow tube 2 is being ejected laterally, and in the desired direction. This may be important, for example, when the bone graft delivery device is placed within a disc space, and bone graft is being ejected laterally from the second end 8 of the hollow tube 2 in a specific direction. In other embodiments, the footing 11 may also serve as a visual marker for the surgeon, as it extends away from the horizontal wall of the hollow tube 2, and is therefore visible at the second end 8 of the hollow tube 2. As shown in FIG. 3, the presence of the footing 11 does not affect the interior slope or curved surface 10A of the hollow tube 2, so that the plunger 12 of the design shown in FIG. 1B may still be used with the hollow tube 2 of this alternate embodiment.

Figure 4:
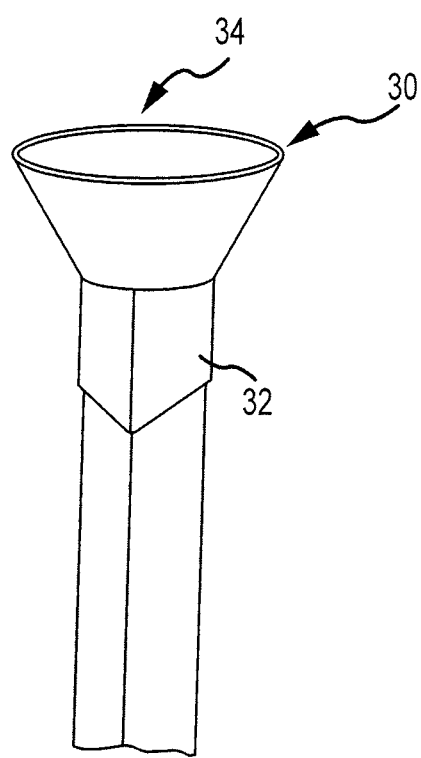
FIG. 4 is a partial perspective view of another alternative embodiment where the tubular portion includes a funnel at its proximal end designed to receive bone graft.

Referring now in detail to FIG. 4, a removable funnel 30 is shown, which comprises an opening 34 which is generally larger in diameter or dimension when compared to the opening 4 of the hollow tube 2. This removable funnel 30 further comprises a sleeve 32, the sleeve 32 having an internal cross-section which is substantially congruent with the external cross-section of the first end 6 of the hollow tube 2. Thus, according to this embodiment, the funnel 30 is selectively removable from the first end 6 of the hollow tube 2, and may allow a surgeon to more easily place new or additional bone graft into the hollow tube 2 by way of the opening 34 of the funnel 30. This funnel 30 may be used in connection with a hollow tube 2 that has been pre-filled with bone graft, or a hollow tube which is not pre-filled with bone graft. Thus, the funnel may be selectively positioned on the first end 6 of the hollow tube 2 at any point during the surgical operation when the surgeon desires new or additional bone graft be placed in the hollow tube 2 of the bone graft delivery device.

Figure 5:
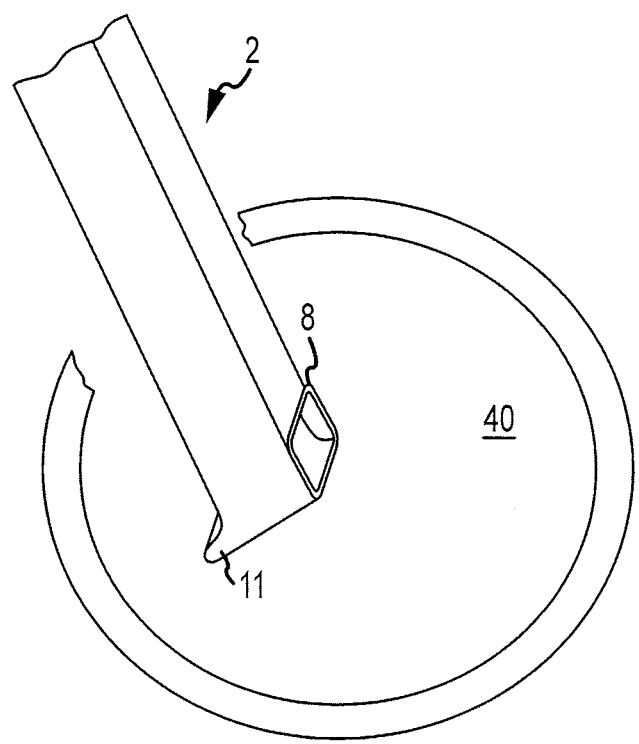
FIG. 5 is a perspective view of the device according to one embodiment where the device is positioned in a disc space during a surgical operation.
Figure 11A:
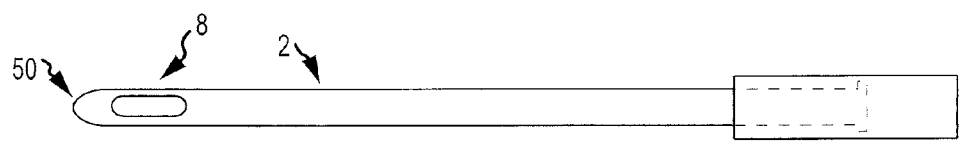
FIG. 11A-D are sequential elevation views of the tubular portion of the device with telescoping feature.
Figure 11B:
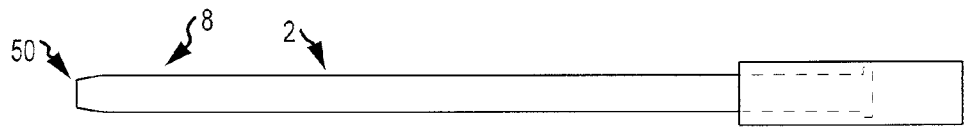
Figure 11C:
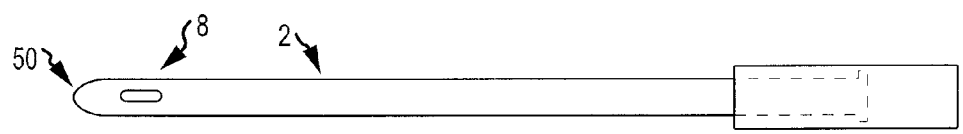
Figure 11D:
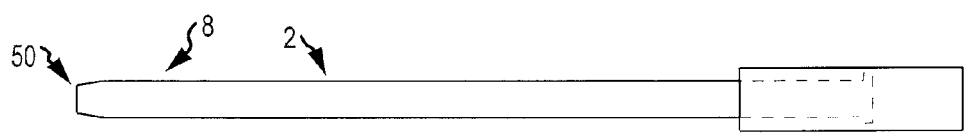

Referring now in detail to FIG. 5, one particular application of the bone graft delivery device is shown in a perspective view. Here, the bone graft delivery device is shown with the embodiment of the hollow tube 2 further comprising a footing 11, and a second end opening for ejecting bone graft in a generally lateral direction, here in the interior of a disc space 40. The disc is shown with an opening on one end for inserting the second end 8 of the hollow tube 2 of the bone graft delivery device. As opposed to prior art bone graft delivery devices which have an opening at a second end that is open to the longitudinal axis of the delivery device, the present invention comprises a lateral opening, which as shown in FIG. 5 allows a surgeon to eject bone mill into the lateral direction and thereby into the opened areas of the disc space 40. A surgeon has the option to rotate the direction of the opening in the second end 8 of the hollow tube 2 for ejecting additional bone graft to other open areas in the disc space 40. Once the disc space 40 is substantially full of bone graft, the surgeon may remove the hollow tube 2 without disturbing the disc or anatomy of the patient. The surgeon may also accomplish the delivery of bone graft without displacing any cage or other structural implantable device which may be present in or adjacent the disc space. One skilled in the art will appreciate that the hollow tube 2 further comprising a footing 11, and a second end opening for ejecting bone graft in a generally lateral direction, may effect the delivery of bone graft in a lateral direction simultaneous with delivery in a longitudinal direction.

Referring now to FIGS. 6-10, a preferred embodiment of the device is shown. In regard to FIG. 6, a bone graft delivery device portion is shown, comprised of a hollow tubular member 2, which has a first proximate end 6 and a second distal end 8, with a general hollow structure therebetween. The generally hollow tube 2 is shown with one of two lateral openings at the distal end 8 of the tubular member 2 viewable (the other is viewable in FIG. 7). Also in FIG. 6, the plunger member 12 is shown. The manner of insertion of plunger member 12 into tubular member 2 is also provided. Thus, as shown in FIG. 6, the hollow tube 2 allows bone graft material to be inserted into the opening 4 at the proximal end 6 of the hollow tube 2, and ultimately exited from the hollow tube 2 through the second distal end 8 from the lateral openings at the distal end 8 of the hollow tubular member 2.

Furthermore regarding FIG. 1, a preferred embodiment of the distal end 10 of the tubular member 2 and the distal end 20 of the plunger member 12 is provided. The configuration provided, a wedge-shaped end 50 of the tubular member and a wedge-shaped end of the plunger 52, allows substantially all of the bone graft material to be removed and thus inserted into the surgical area when the plunger 2 is fully inserted into the tubular member 2. The wedge-shaped feature 50 of the distal end 10 of the tubular member 2 and the wedge-shaped end 52 of the distal end 20 of the plunger member 12 is discussed in additional detail with respect to FIGS. 3 and 4 below. The ability to remove substantially all of the bone graft material is an important feature of the invention because bone graft material is traditionally expensive and may require surgery to obtain.

Referring now to FIG. 2, a perspective view of a preferred embodiment of the hollow tubular member 2 is provided. Consistent with FIG. 6, the generally hollow tube 2 is shown with one of two lateral openings at the distal end 8 of the tubular member 2 viewable (the other is viewable in FIG. 6). Thus, in operation the hollow tube 2 allows bone graft material to be inserted into the opening 4 at the proximal end 6 of the hollow tube 2, and ultimately exited from the hollow tube 2 through the second distal end 8 from the lateral openings at the distal end 8 of the hollow tubular member 2. In this configuration, bone graft material is ejected into the surgical area in two lateral directions. One skilled in the art will appreciate that the openings at the distal end 8 of the hollow tubular member 2 need not be positioned exclusively on one or more lateral sides of the distal end 8 of the tubular member to allow bone graft material to be provided to the surgical site in other than a purely axial or longitudinal direction. Further, one skilled in the art will appreciate that the specific absolute and relative geometries and numbers of lateral openings may vary, for example the distal end 8 of the tubular member 2 may have more than two openings that are of different shape (e.g. oval, rectangular).

Referring now to FIG. 8, an elevation view of the wedge-shaped distal end 50 of the tubular member 2 is provided. In this embodiment, the proximal end of the plunger would conform to the same shape, to allow close fitting of the plunger and the hollow tubular member. This contoured plunger, corresponding to the contoured tubular member, serves several purposes: First, it maintains the plunger in a desirable rotational position with respect to the hollow tube (i.e., prevent the plunger from inadvertently or intentionally being manipulated to rotate about the longitudinal axis of the hollow tube); Second, it ensure that when the plunger is fully inserted, the plunger removes substantially all of the bone graft material from the hollow tube. Also, the contoured plunger, corresponding to the contoured tubular member, allows immediate identification of the orientation of the device, and more specifically the direction of eject of the bone graft material into the surgical area. One skilled in the art will appreciate that the plunger need not terminate in a wedge-shape surface to effect the substantial removal of all of the bone graft material placed into the hollow tube; more specifically, any shape that allows conformance between the internal contour of the distal end of the hollow tube and the distal end of the plunger will effect the substantial removal of the bone graft material.

Referring now to FIG. 9, an elevation view of the opening 4 of the distal end 6 of the hollow tubular member 2 is provided. As shown in FIG. 9, the opening 4 at the proximal end 6 of the hollow tube 2 allows deposit of bone graft material. In this configuration, the cross-section of the opening 4 at the proximal end 6 of the hollow tube 2 is generally square. Although a generally square cross-section is depicted, the cross-section need not be limited to a generally square shape. For example, cross-sections of an oval shape or those with at least one defined angle to include obtruse, acute, and right angles can provide a shape in some situations that is more congruent with the size or shape of the annulotomy of a particular disc space.

Referring to FIGS. 10A-D, sequential elevation views of the square-shaped embodiment of the device is provided, depicting the complete insertion of the plunger 12 into the hollow tubular member 2. In each of FIGS. 10A-D, the wedge-shaped distal end 50 of the tubular member 2 is depicted. Also, each of FIGS. 10A-D depict the additional length of the plunger element 12 when inserted into the tubular member 2. FIG. 10A shows one of two lateral openings at the distal end 8 of the hollow tubular member 2. FIG. 10C shows another of the two lateral openings at the distal end 8 of the hollow tubular member 2. One skilled in the art will appreciate that the openings at the distal end 8 of the hollow tubular member 2 need not be positioned exclusively on one or more lateral sides of the distal end 8 of the tubular member to allow bone graft material to be provided to the surgical site in other than a purely axial or longitudinal direction. Further, one skilled in the art will appreciate that the specific absolute and relative geometries and numbers of lateral openings may vary, for example the distal end 8 of the tubular member 2 may have more than two openings that are of different shape (e.g. oval, rectangular).

The instruments used with the bone graft delivery device described above in its varying embodiments may include one or more tamps, preferably having a configuration which at least in part corresponds in shape and contour of the hollow tube portion of the delivery device. The one or more tamps may be adapted to correspond further to the shape and contour of the graspable end of the plunger, for use in driving the plunger through the hollow tube portion of the delivery device to ensure any remaining bone graft located in the hollow tube is delivered to the graft receiving area.

A bone graft tamping device may also be provided, which is adapted to be telescopically inserted into the hollow tube after the plunger is removed from the hollow tube. The bone graft tamping device, according to this embodiment, may include one or more longitudinal channels along the outer circumference of the bone graft packer for permitting any trapped air to flow from the bone graft receiving area to the graspable end of the hollow tube during packing of bone graft. The bone graft packer may further include a handle at one end designed ergonomically for improving ease of use. The bone graft packer in this embodiment thereby facilitates packing of bone graft within the hollow tube.

The hollow tube may also be fitted with a passageway wherein a surgical tube or other device may be inserted, such as to deliver a liquid to the surgical area or to extract liquid from the surgical area. In such an embodiment, the plunger is adapted in cross-section to conform to the hollow tube's cross-section.

In another embodiment of the present invention, a kit of surgical instruments comprises a plurality of differently sized and/or shaped hollow tubes and a plurality of differently sized and/or shaped plungers. Each of the plungers correspond to at least one of the hollow tubes, whereby a surgeon may select a hollow tube and a plunger which correspond with one another depending upon the size and shape of the graft receiving area and the amount or type of bone graft to be implanted at such area. The corresponding hollow tubes and plungers are constructed and arranged such that bone graft can be placed within the hollow tubes with the plungers, and inserted nearly completely into the hollow tubes for removing substantially all of the bone graft material from the hollow tubes, such as in the preferred embodiments for the plunger described above. The use of more than one hollow tube/plunger combination permits at least two different columns of material to be selectably delivered to the targeted site, e.g. one of bone graft material from the patient and another of Bone Morphogenetic Protein (BMP), or e.g. two different types of bone graft material or one delivering sealant or liquid. Also, one or both hollow tubes could be preloaded with bone graft material.

The kit of surgical instruments may comprise a plurality of differently sized and/or shaped graft retaining structures, each corresponding to at least one hollow tube and at least one plunger.

The bone graft receiving area can be any area of a patient that requires delivery of bone graft. In the preferred embodiment, the bone graft is delivered in a partially formed manner, and in accordance with another aspect of the present invention, requires further formation after initial delivery of the bone graft.

Another embodiment of the present invention provides a method by which a hollow tube and a plunger associated with the hollow tube are provided to facilitate delivery of the bone graft to a bone graft receiving area.

According to one embodiment, the present invention provides a bone graft delivery system, by which a hollow tube and/or plunger assembly may be prepared prior to opening a patient, thus minimizing the overall impact of the grafting aspect of a surgical implantation or other procedure. Moreover, the hollow tube may be made to be stored with bone graft in it for a period of time, whether the tube is made of plastic, metal or any other material. Depending upon the surgical application, it may be desirable to only partially fill the tube for storage, so that a plunger can be at least partially inserted at the time of a surgery.

Thus, the bone graft delivery device may either come with a pre-filled hollow tube, or a non-filled hollow tube, in which the surgeon will insert bone graft received from the patient (autograft), or from another source (allograft). In either case, the surgeon may first remove any wrapping or seals about the hollow tube, and/or the pre-filled bone graft, and insert the hollow tube into the patient such that the second end of the hollow tube is adjacent the bone graft receiving area. Once the hollow tube is in place, and the opening at the second end of the hollow tube is oriented in the direction of the desired placement of bone graft, the surgeon may then insert the second end of the plunger into the opening at the first end of the hollow tube, and begin pressing the second end of the plunger against the bone graft material in the hollow tube. In this fashion, the plunger and hollow tube cooperate similar to that of a syringe, allowing the surgeon to steadily and controllably release or eject bone graft from the second end of the hollow tube as the plunger is placed farther and farther into the opening in the hollow tube. Once the desired amount of bone graft has been ejected from the hollow tube (for in some instances all of the bone graft has been ejected from the hollow tube) the surgeon may remove the plunger from the hollow tube, and complete the surgery. In certain operations, the surgeon may elect to place additional bone graft into the hollow tube, and repeat the steps described above. Furthermore, the pre-filled bone graft elements may be color-coded to readily identify the type of bone graft material contained therein.

According to the embodiment described in the preceding paragraph, the present invention may be carried out by a method in which access is provided to a graft receiving area in a body, bone graft is placed into a hollow tube having a first end and a second end, the hollow tube, together with the bone graft, is arranged so that the first end of the hollow tube is at least adjacent to the graft receiving area and permits lateral or nearly lateral (n relation to the longitudinal axis of the hollow tube and plunger assembly) introduction of bone graft to the graft receiving area. This method prevents loss of bone graft due to improper or limited orientation of the bone graft delivery device, and further allows a user to achieve insertion of a desired quantity of bone graft by way of the contoured plunger and hollow tube configuration described according to preferred embodiments herein.

The method of the present invention may also be carried out by providing a hollow tube having a first end and a second end, constructed so that it may receive a measurable quantity of bone graft, and so that the first end may be arranged at least adjacent to a bone graft receiving area, and so that bone graft can be delivered from the first end of the hollow tube through the second end of the hollow tube and eventually to the bone graft receiving area upon movement of the plunger in a generally downward direction through the hollow tube (i.e., in a direction from the first end to the second end). According to this embodiment, a graft retaining structure may also be provided for use in connection with the contoured edge of the plunger, such that the graft retaining structure is positioned between the contoured edge of the plunger and the bone graft, but which is adhered to the bone graft and remains at the graft receiving area following removal from the hollow tube. Furthermore, this graft retaining structure may also be employed with another tool, such as a graft packer, which is employed either before or after the hollow tube is removed from the graft receiving area.

In another embodiment, the one or more plungers corresponding to the one or more hollow tubes are positioned with distal ends near the proximate end of the horizontal tube before use, said plungers having a detent to retain plunger in ready position without undesired movement before surgeon chooses which one or more plungers to extend through hollow horizontal tube and deliver bone graft material and/or desired material to the surgical area.

According to another embodiment of the present invention, a hollow tube and plunger assembly is provided in which the hollow tube and/or the plunger assembly is disposable. Alternatively, the tube may be made of a biocompatible material which remains at least partially in the patient without impairing the final implantation. Thus, the hollow tube may be formed from a material that is resorbable, such as a resorbable polymer, and remain in the patient after implantation, so as not to interfere with the growth of the bone or stability of any bone graft or implant.

The current design preferably comprises a hollow tubular member comprising a rounded edge rectangular shaft, which may be filled or is pre-filled with grafting material. The loading is carried out by the plunger. The rectangular design is preferable as it allows the largest surface area device to be placed into the annulotomy site of a disk, but in other embodiments may be formed similar to conventional round shafts. The other preferred feature includes a laterally-mounted exit site for the graft material. The combination of this design feature allows direction-oriented dispersion of the graft material. This allows ejection of the graft material into an empty disk space as opposed to below the hollow tube, which would tend to impact the material and not allow its spread through a disk space.

Another feature of this design is that a rectangular design allows the user to readily determine the orientation of the device and thereby the direction of entry of the bone graft material into the surgical area. However, such a feature may be obtained alternatively through exterior markings or grooves on the exterior on the hollow tube. Such exterior grooves or markings would allow use of a range of cross-sections for the device, to include a square, circle, or oval while allowing the user to readily determine the orientation of the device relative to the direction of entry of the bone graft material into the surgical area.

A further feature of this design is that an anti-perforation footing or shelf is paced on the bottom of the hollow tube to prevent annular penetration and/or injury to the patient's abdomen or other anatomy adjacent the bone graft receiving area.

Another alterative embodiment to the design described herein includes a removable funnel attachment. This allows easy loading of the cannula with the funnel and with its removal easy visualization of the operating site without visual blockage through the microscope.

In another embodiment of the invention, all or some of the elements of the device or sections of all or some of the device may be disposable. Disposable medical devices are advantageous as they typically have reduced recurring and initial costs of manufacture.

In another embodiment of the device, the distal tip or end of the plunger device is composed of a different material to the rest of the plunger, so as the material at the distal end of the plunger is sponge-like or softer-than or more malleable than the rest of the plunger so as upon engagement with the interior distal end of the hollow tube, the distal end of the plunger substantially conforms to the interior configuration of the hollow tube. Similarly, the plunger distal end may be made of a material that is adaptable to substantially conform to the interior shape of the distal end of the hollow tube. Such configurations enable substantially all of the material contained within the plunger to be delivered to the targeted site.

Another alterative embodiment to the design described herein includes a navigation aid on one or more surfaces of the tubular body to permit surgeon to know how far the device has been inserted or to ensure proper alignment relative to a transverse bone graft delivery site (i.e. disc space). Such capability is particularlty important when the patient or surgical area is not positioned immediately below the surgeon, or multiple procedures are being performed. A navigation aid allows more immediate and reliable locating of the surgical area for receiving of bone graft material. In one embodiment, the hollow tube is scored or marked or provides some affirmative indication, actively or passively, to the surgeon to indicate degree of delivery of the material, e.g. bone graft material, to the delivery site, and/or position of the plunger element. For example, the exterior of the hollow tube could be color-coded and/or provided with bars. In another embodiment, a computer and/or electro-mechanical sensor or device is used to provide feedback to the surgeon to indicate degree of delivery of the material, e.g. amount of cc's of bone graft material, to the delivery site, and/or position of the plunger element.

In another alterative embodiment to the design described herein, the plunger could include an activation device, which is often in a liquid or semi-liquid state, and that may be injected once the semi-solid portion of the morphogenic protein has been displaced by the movement of the plunger through the tubular body. That is, the plunger pushes the dry material, and once completed has a bulb or other device on the usable end to insert the liquid portion of the activating agent through the inner lumen within the plunger to evacuate the liquid from the plunger and out an opening at the non-usable end of the plunger so as to contact the dry material already inserted into the disc space)

To provide further clarity to the Detailed Description provided herein in the associated drawings, the following list of components and associated numbering are provided as follows:

REFERENCE NO. COMPONENT

2 Hollow tube
4 Opening (of Hollow tube)
6 First end (of Hollow tube)
8 Second end (of Hollow tube)
10 Curved surface (of Hollow tube)
10A Curved interior surface (of Hollow tube)
11 Footing (of Hollow tube)
12 Plunger
16 Handle (of Plunger)
18 Second end (of Plunger)
19 Horizontal surface (of Plunger)
20 Curved surface (of Plunger)
30 Funnel
32 Sleeve (of Funnel)
34 Opening (of Funnel)
40 Disc space
A Height of opening (in Hollow tube)
B Width of opening (in Hollow tube)
50 Wedge-shaped Second end (of Hollow tube)
52 Wedge-shaped Second end (of Plunger)

While various embodiment of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A bone graft insertion apparatus comprising:
a hollow tube constructed to receive bone graft, said hollow tube having an extended axis and a proximal end and a distal end, said hollow tube having a generally uniform interior rectangular cross-section from said proximal end to said distal end, said distal end having an interior tapered surface, said distal end having two symmetrical lateral openings, said two symmetrical lateral openings of an oval racetrack shape comprising two pairs of edges wherein a first pair of edges are straight and a second pair of edges are semi-circular; and
a plunger adapted for inserting into said proximal end of said hollow tube along the extended axis, said plunger having a distal end exterior surface of rectangular cross-section contoured to said interior rectangular cross-section of said hollow tube, said plunger distal end exterior surface forming a congruent fit with said hollow tube uniform interior cross-section,
wherein the distal end of said plunger is configured to remain always proximal to the distal end of said hollow tube when said plunger is inserted into said hollow tube,
wherein said hollow tube and said plunger are configured to deliver bone graft material into a surgical site through the two symmetrical lateral openings when the plunger is advanced from the proximal end to the distal end of the hollow tube along the extended axis.

2. The apparatus according to claim 1, wherein said distal end of said plunger is positioned opposite said two symmetrical lateral openings when the plunger is fully advanced from the proximal end to the distal end of the hollow tube along the extended axis.

3. The apparatus according to claim 1, further comprising:
a detachable funnel adapted to connect to said proximal end of said hollow tube, wherein said detachable funnel facilitates insertion of said bone graft into said hollow tube.

4. The apparatus of claim 1, whereby when said plunger is inserted into said hollow tube, said plunger is substantially prevented from rotating.

5. The apparatus of claim 1, wherein said distal end of said hollow tube comprises a closed distal tip.

6. The apparatus of claim 1, wherein said distal end of at least one of said plunger and said hollow tube are constructed of material more flexible than material comprising said proximal end of said hollow tube, whereby the risk of injury to the patient is reduced.

7. The apparatus of claim 1, wherein said hollow tube is preloaded with one of bone graft and bone morphogenic protein.

8. The apparatus of claim 1, wherein the hollow tube has at least one telescoping portion.

9. A bone graft insertion apparatus comprising:
a hollow tube constructed to receive bone graft, said hollow tube having a proximal and distal end, said hollow tube having a generally uniform interior rectangular cross-section from said proximal end to said distal end;
whereby said distal end of said hollow tube comprises two symmetrical lateral openings, said two symmetrical lateral openings of an oval racetrack shape comprising two pairs of edges wherein a first pair of edges are straight and a second pair of edges are semi-circular;
a plunger adapted for insertion within said hollow tube at said proximal end of said hollow tube;
whereby said plunger is constructed and arranged with respect to said hollow tube so as to present at least one substantially flat contour;
whereby said plunger has a distal end exterior surface of rectangular cross-section contoured to said interior rectangular cross-section of said hollow tube, said plunger distal end exterior surface forming a congruent fit with said hollow tube uniform interior cross-section, wherein movement of said plunger from said proximal to said distal end of said hollow tube removes substantially all of said bone graft received by said hollow tube;
whereby said bone graft is delivered to a graft receiving area.

10. The apparatus according to claim 9, further comprising communication between said proximal end of said hollow tube and said graft receiving area, wherein said communication is at least one of electrical and mechanical.

11. The apparatus according to claim 9, wherein the distal end of said plunger is configured to remain always proximal to the distal end of said hollow tube when said plunger is inserted into said hollow tube.

12. The apparatus according to claim 9, further comprising:
a detachable funnel positioned at said proximal end of said hollow tube, wherein said detachable funnel facilitates insertion of said bone graft into said hollow tube.

13. The apparatus of claim 9, further comprising:
a sloped or curved surface on said interior surface of said distal end of said hollow tube, said sloped or curved surface positioned substantially adjacent and opposite to said two symmetrical lateral openings.

14. The apparatus of claim 1, wherein said two symmetrical lateral openings are configured with a minor length and a major length, said minor length between 4 mm and 9 mm, and said major length between 7 mm and 14 mm.

15. The apparatus of claim 9, wherein said two symmetrical lateral openings are configured with a minor length and a major length, said minor length between 4 mm and 9 mm, and said major length between 7 mm and 14 mm.

16. A bone graft insertion apparatus comprising:
a hollow tube constructed to receive bone graft, said hollow tube having an extended axis and a proximal end and a distal end, said hollow tube having a generally uniform interior and exterior rectangular cross-section from said proximal end to said distal end, said distal end having a closed distal wedge-shaped tip, said distal end having two symmetrical lateral openings, said two symmetrical lateral openings of an oval racetrack shape comprising two pairs of edges wherein a first pair of edges are straight and a second pair of edges are semi-circular;
a plunger adapted for inserting into said proximal end of said hollow tube along the extended axis, said plunger having a distal end exterior surface of rectangular cross-section contoured to said interior rectangular cross-section of said hollow tube, said plunger distal end exterior surface forming a congruent fit with said hollow tube uniform interior cross-section, wherein movement of said plunger from said proximal to said distal end of said hollow tube removes substantially all of said bone graft received by said hollow tube, wherein the two symmetrical lateral openings substantially preclude the delivery of bone graft material directly along the axis of the hollow tube, said plunger precluded from rotating when inserted into said hollow tube;
wherein the distal end of said plunger is configured to remain always proximal to the distal end of said hollow tube when said plunger is inserted into said hollow tube,
wherein said two symmetrical lateral openings are configured with a minor length and a major length, said minor length between 4 mm and 9 mm, and said major length between 7 mm and 14 mm.

\* \* \* \* \*